United States Patent [19]
Miki et al.

[11] Patent Number: 5,925,534
[45] Date of Patent: Jul. 20, 1999

[54] METHOD FOR MEASURING LDL-CHOLESTEROL

[75] Inventors: Yutaka Miki; Isao Koyama; Nobuko Imajo; Masayuki Futatsugi; Toshiro Hanada, all of Osaka, Japan

[73] Assignee: Wako Pure Chemical Industries, Ltd., Osaka, Japan

[21] Appl. No.: 09/128,930

[22] Filed: Aug. 5, 1998

[30] Foreign Application Priority Data

Jun. 8, 1998 [JP] Japan .................................. 10-175396

[51] Int. Cl.$^6$ ............................... C12Q 1/60; C12Q 1/32; C12Q 1/00
[52] U.S. Cl. .................................. 435/11; 435/26; 435/25; 435/4; 435/19; 435/28; 536/46; 536/103; 536/1.11
[58] Field of Search .................................. 435/11, 26, 25, 435/4, 19, 28; 536/46, 103, 1.11

[56] References Cited

U.S. PATENT DOCUMENTS 5,814,472   9/1998   Miki et al. ................................ 435/11

*Primary Examiner*—Louise N. Leary
*Attorney, Agent, or Firm*—Armstrong, Westerman, Hattori, McLeland & Naughton

[57] ABSTRACT

The amount of cholesterol in low density lipoproteins in a sample can be measured by contacting the sample with one or more reagent solutions to carry out the reaction in the presence of a polyanion and an amphoteric surfactant, followed by optical measurement of the reaction product.

33 Claims, 13 Drawing Sheets

METHOD FOR MEASURING LDL-CHOLESTEROL

BACKGROUND OF THE INVENTION

1. Field of the Invention

This invention relates to a method for measuring cholesterol in low density lipoproteins (hereinafter abbreviated as "ULDL") present in samples derived from living bodies, such as serum, plasma, etc., and a reagent, a reagent composition and a kit which are used for practicing said method.

2. Description of the Related Art

Major components of lipids in serum are cholesterol, triglycerides, phospholipids, etc. These serum lipids bind to apoproteins to form lipoproteins which circulate in the blood. The lipoproteins can be classified by differences in density into high density lipoproteins (HDL), low density lipoproteins (LDL), very low density lipoproteins (VLDL), chylomicrons (CM), etc. Among these lipoproteins, HDL has a function of carrying excess cholesterol deposited on tissues to a liver, and has an anti-arteriosclerotic action. On the other hand, LDL is a major carrier of cholesterol from a liver to each tissue. An increase of LDL seems to have an intimate relation to generation of arteriosclerosis.

Therefore, the cholesterol in LDL (hereinafter abbreviated as "LDL-cholesterol") is regarded as a risk factor for arteriosclerosis and ischemic heart disease (coronary arteriosclerotic disease). Thus, the content of LDL-cholesterol is an important indicator of diagnosis, therapy and prophylaxis of these diseases.

As methods for measuring LDL-cholesterol, there have been known a precipitation method, an ultracentrifugal method, an electrophoresis method, and a Friedewald method. Among these methods, the precipitation method, the ultracentrifugal method and the electrophoresis method have complicated procedures due to pretreatment steps such as separation of LDL from unnecessary lipoproteins other than LDL by precipitation/ultracentrifugation treatments, ultracentrifugation treatment or electrophoresis treatment. Thus, these methods are disadvantageous in that direct measurement using only an autoanalyzer which is widely used in the field of clinical tests is impossible.

On the other hand, according to the Friedewald method known by the Friedewald equation, wherein a total cholesterol value, a HDL-cholesterol value and a triglyceride value are used for computation, it has a problem in that measurement of an accurate LDL-cholesterol amount is impossible in the case of using a sample containing 400 mg/dl or more of triglycerides.

In order to solve the above-mentioned problems, various methods have been developed in recent years. One of them is, for example, the method disclosed in JP-A 7-280812.

This method comprises agglutinating LDL using a agglutinant and/or an antibody, eliminating (consuming) cholesterol contained in lipoproteins other than LDL by introducing it into another reaction system not pertaining to the quantitative reaction, dissolving the agglutinated LDL to such a degree that the quantitative reaction can be carried out, by use of a surfactant and/or an inorganic salt, and measuring the absorbance of the solution by subjecting the LDL-cholesterol to the quantitative reaction.

But since this method employs a three-reagent system or a four-reagent system at the measurement, it can only be applied to a few autoanalyzers which permit employment of such multi-reagent systems. Many autoanalyzers usually used for clinical tests cannot be used for carrying out the measurement by said method because these autoanalyzers can be used for a one-reagent method or a two-reagent method. Further, said method is disadvantageous also in that since a number of reagents are used, reproducibility of measured values is lowered.

As a method for measuring LDL-cholesterol without a troublesome pretreatment, there is the method disclosed in JP-A 58-165800. This method, however, cannot be a practical measuring method for the following reasons: since the using concentrations of, for example, a surfactant and cholesterol esterase (hereinafter abbreviated as "CHE") in reagents are limited, the preparation of the reagents is troublesome; measuring conditions such as pH at the time of measurement, intervals of measuring times, etc. should be strictly set; and since the cholesterol in HDL reacts to some extent, the LDL-cholesterol can be measured only by a kinetic measurement, i.e., a rate assay.

BRIEF SUMMARY OF THE INVENTION

In view of such circumstances, it is an object of the present invention to provide a method which makes it possible to measure the amount of LDL-cholesterol in a sample derived from a living body, directly using an autoanalyzer or the like without a troublesome pretreatment for separating LDL from unnecessary lipoproteins other than LDL which should be carried out in conventional methods; and a reagent used in said method.

The present invention provides a method for measuring the amount of cholesterol in low density lipoproteins in a sample, which comprises contacting the sample with one or more reagent solutions to carry out the reaction in the presence of a polyanion and an amphoteric surfactant, and subjecting the reaction product obtained above to an optical measurement to determine the amount of cholesterol.

The present invention further provides a reagent composition and a kit which are used in the above-mentioned method.

DETAILED DESCRIPTION OF THE INVENTION

Figure 1:
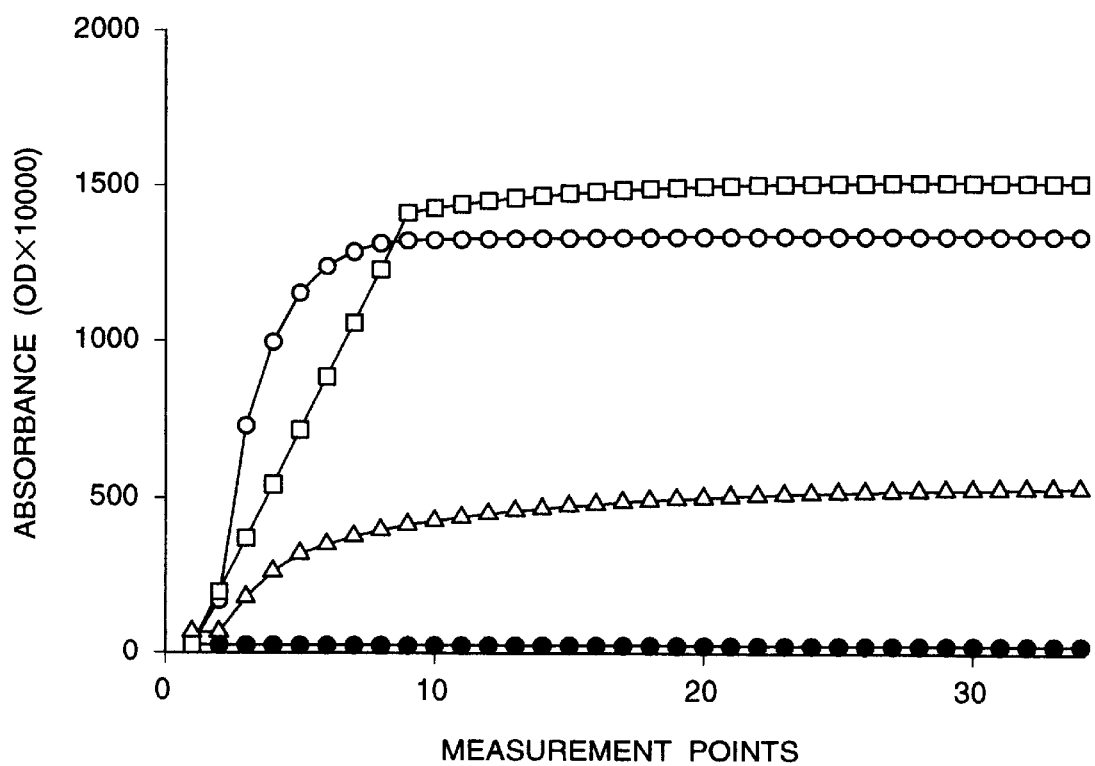
FIG. 1 is a graph showing reaction curves obtained for various lipoprotein fraction samples in Example 1 by use of reagent solution 1.
Figure 2:
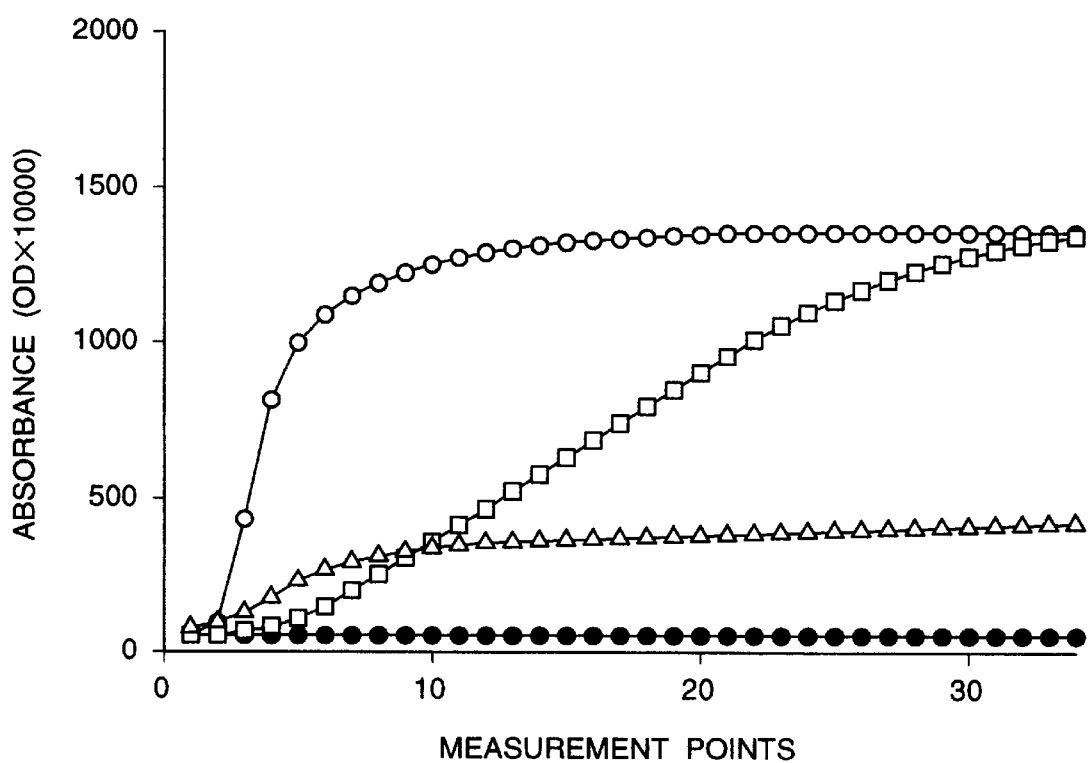
FIG. 2 is a graph showing reaction curves obtained for various lipoprotein fraction samples in Example 1 by use of reagent solution 2.
Figure 3:
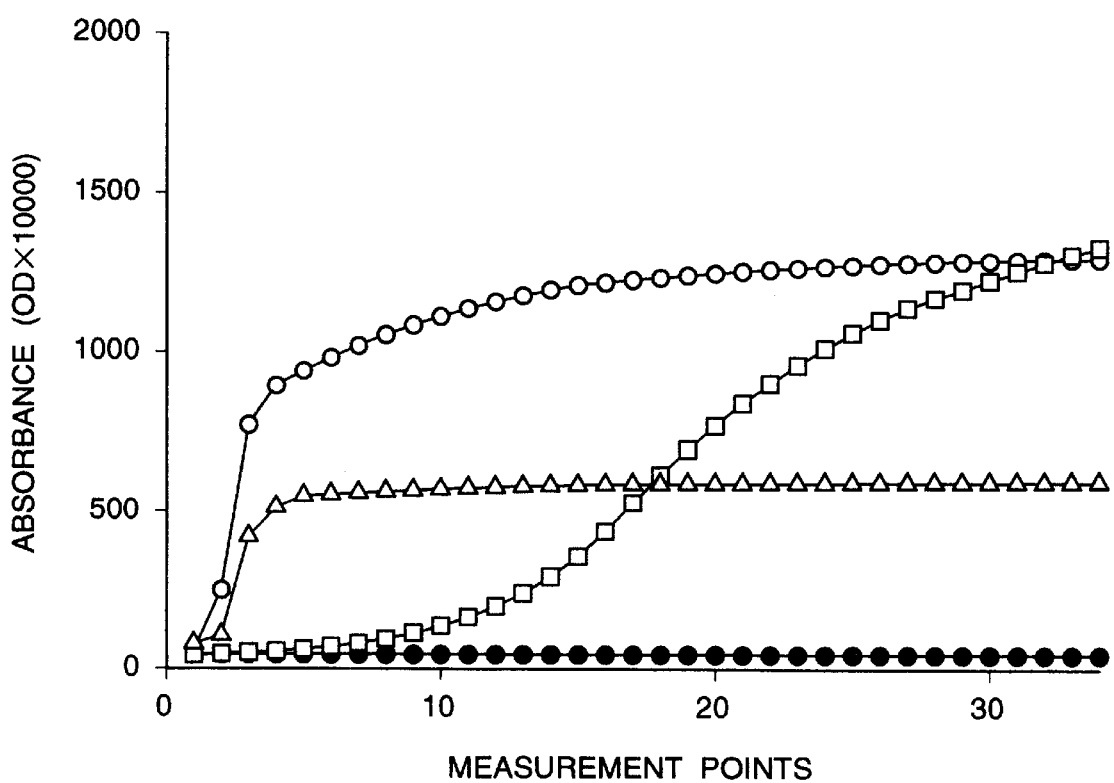
FIG. 3 is a graph showing reaction curves obtained for various lipoprotein fraction samples in Example 1 by use of reagent solution 3.
Figure 4:
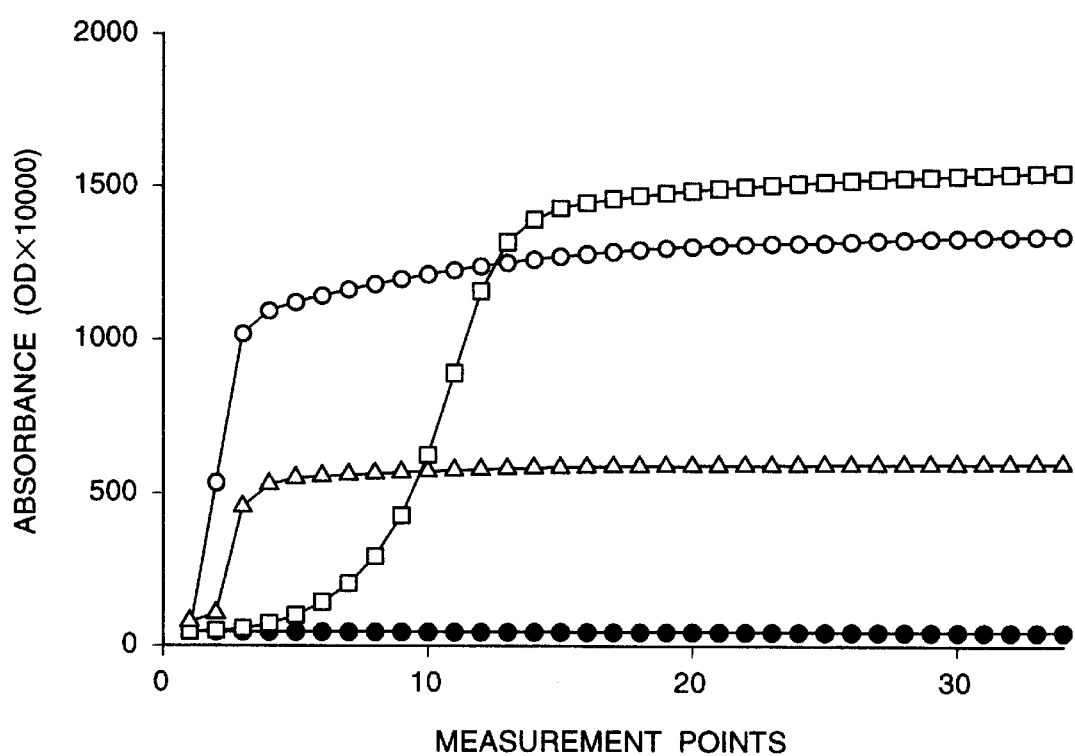
FIG. 4 is a graph showing reaction curves obtained for various lipoprotein fraction samples in Example 1 by use of reagent solution 4.
Figure 5:
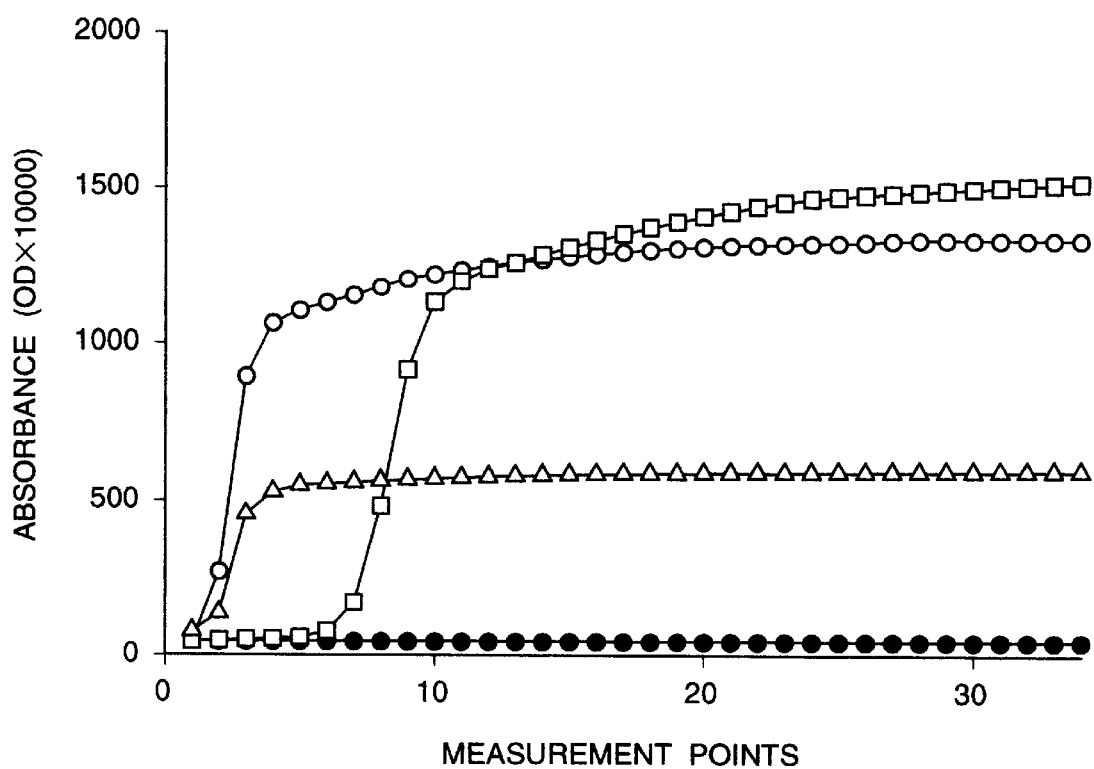
FIG. 5 is a graph showing reaction curves obtained for various lipoprotein fraction samples in Example 1 by use of reagent solution 5.
Figure 6:
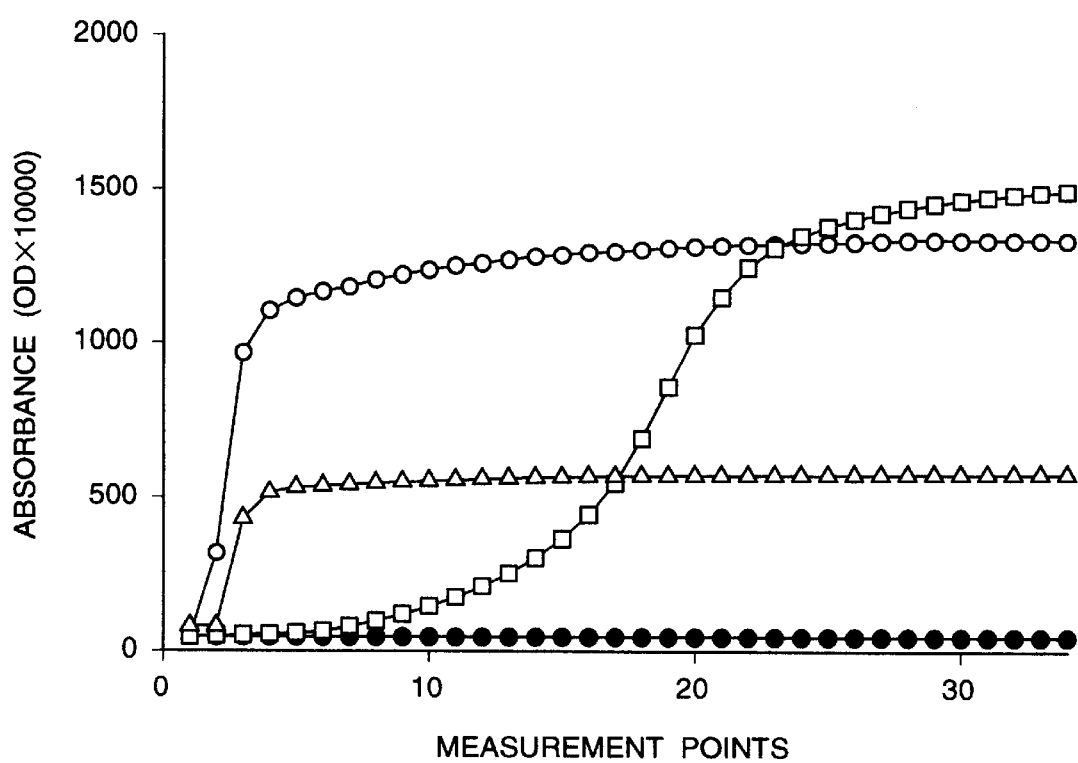
FIG. 6 is a graph showing reaction curves obtained for various lipoprotein fraction samples in Example 1 by use of reagent solution 6.
Figure 7:
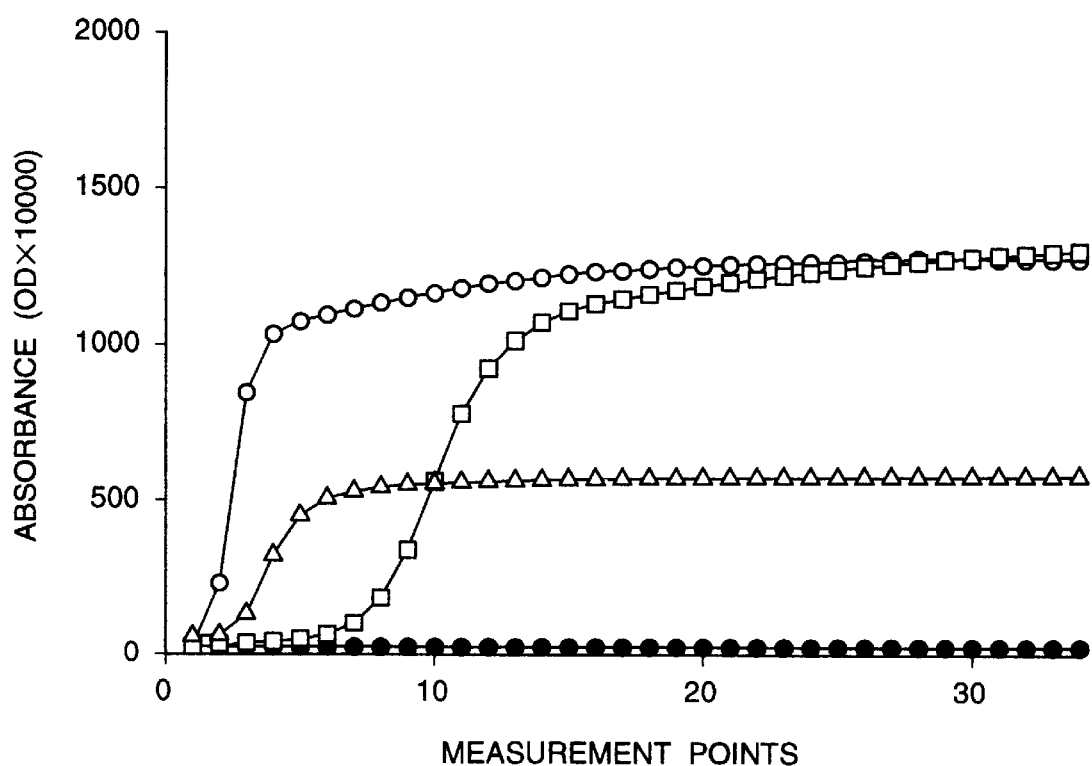
FIG. 7 is a graph showing reaction curves obtained for various lipoprotein fraction samples in Example 1 by use of reagent solution 7.
Figure 8:
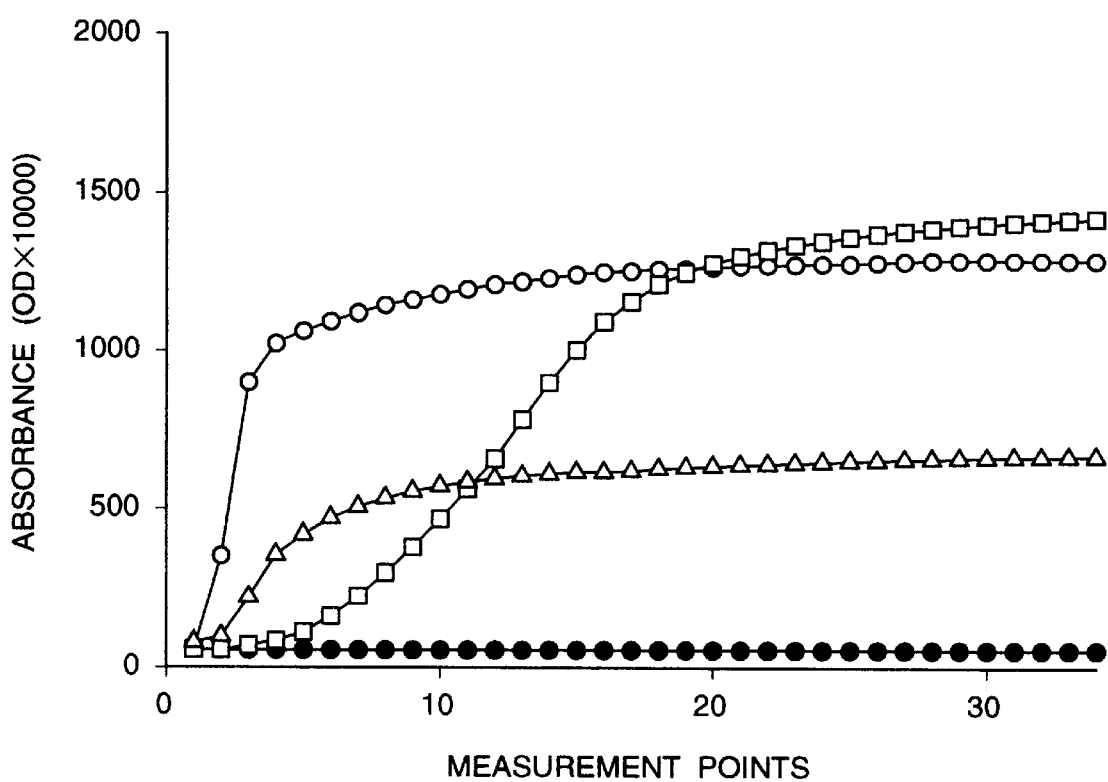
FIG. 8 is a graph showing reaction curves obtained for various lipoprotein fraction samples in Example 1 by use of reagent solution 8.
Figure 9:
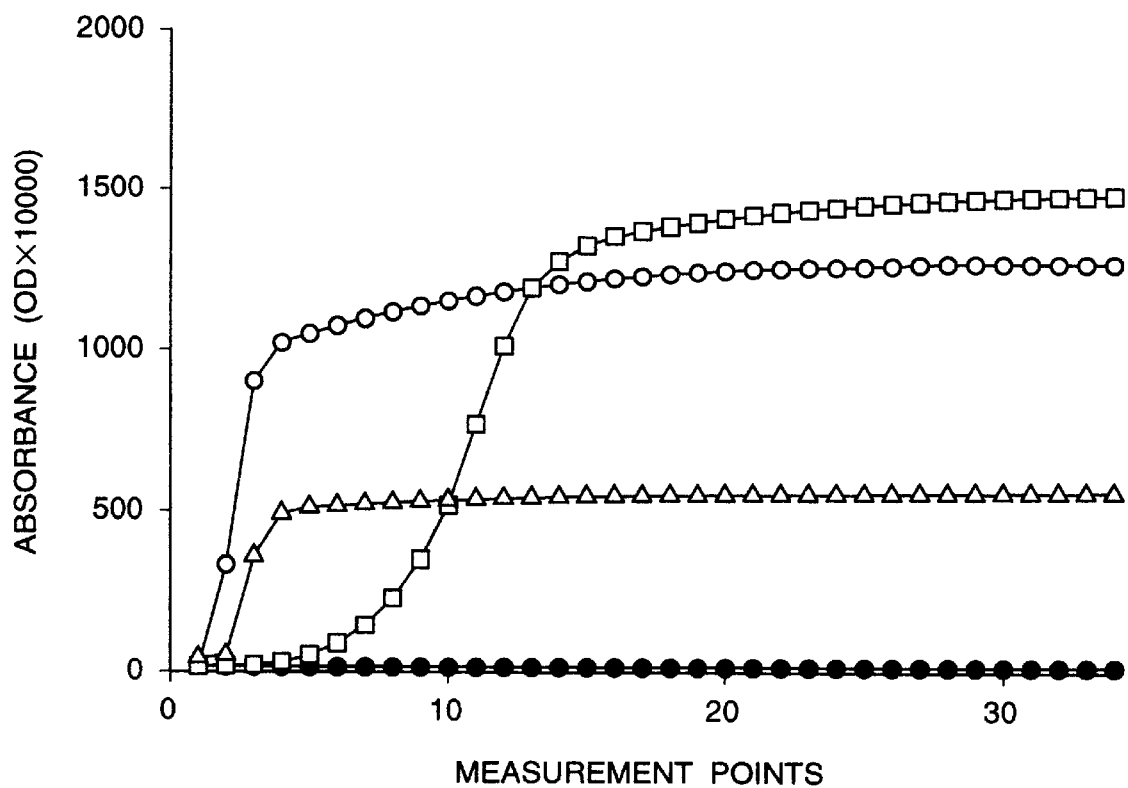
FIG. 9 is a graph showing reaction curves obtained for various lipoprotein fraction samples in Example 1 by use of reagent solution 9.
Figure 10:
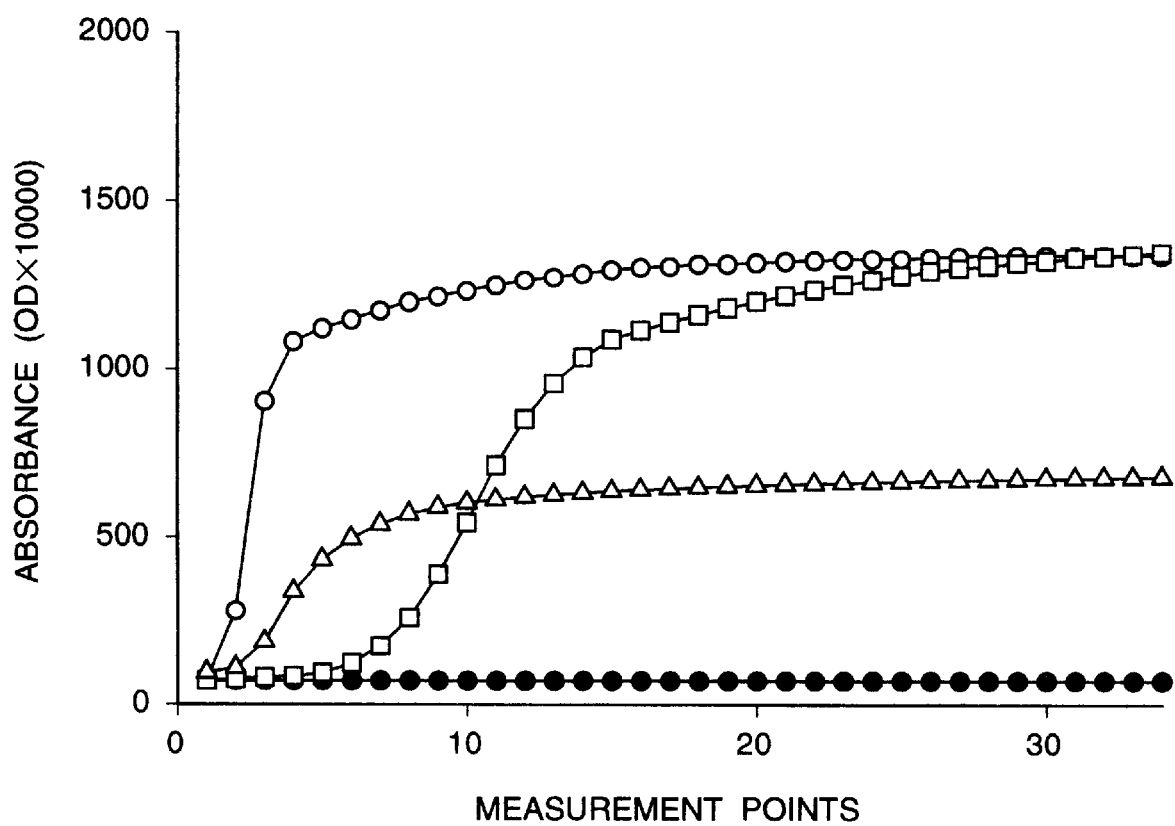
FIG. 10 is a graph showing reaction curves obtained for various lipoprotein fraction samples in Example 1 by use of reagent solution 10.
Figure 11:
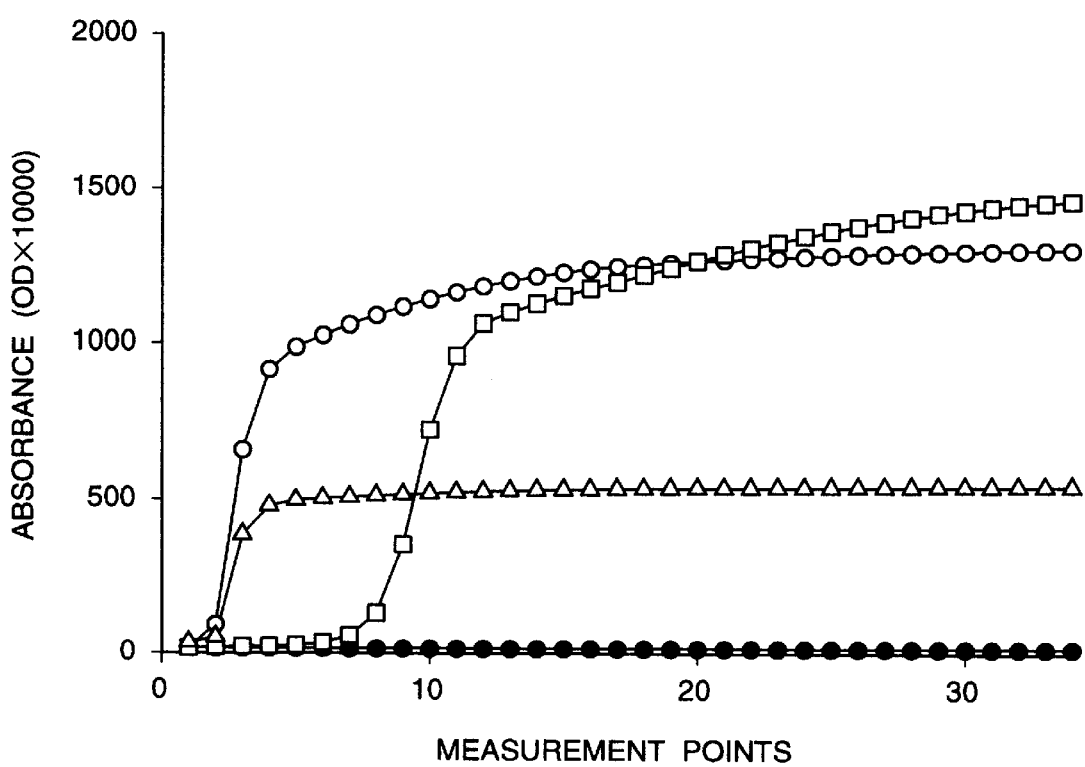
FIG. 11 is a graph showing reaction curves obtained for various lipoprotein fraction samples in Example 1 by use of reagent solution 11.
Figure 12:
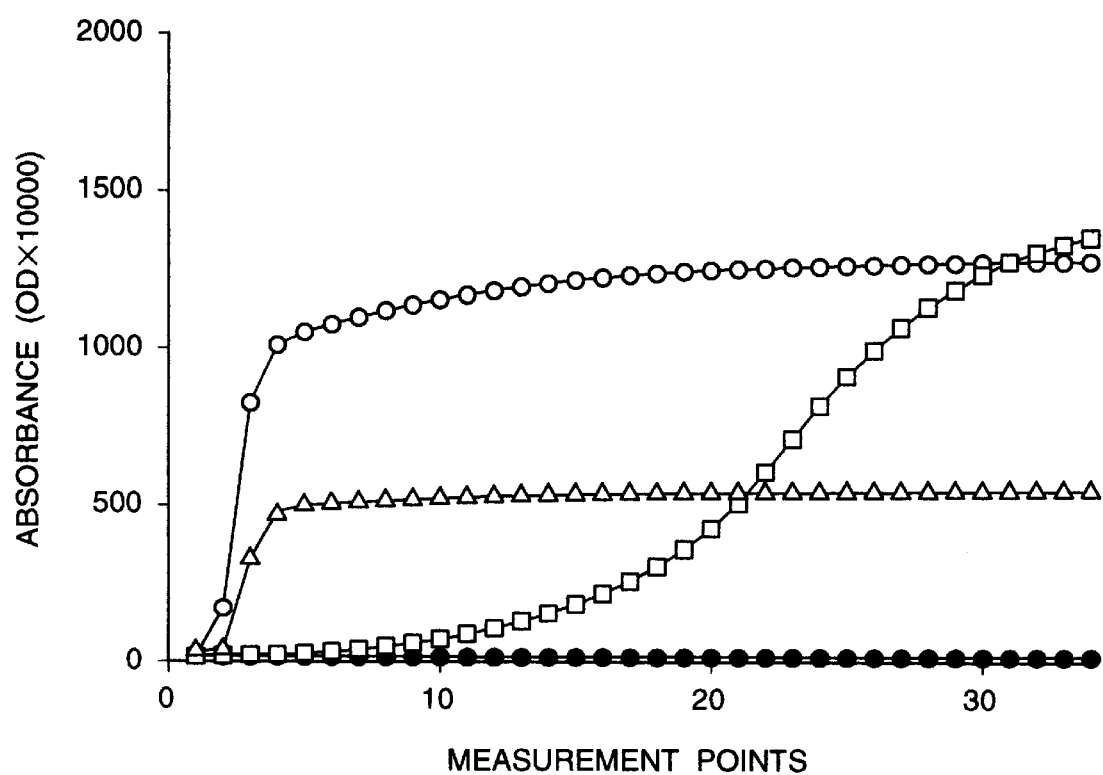
FIG. 12 is a graph showing reaction curves obtained for various lipoprotein fraction samples in Example 1 by use of reagent solution 12.
Figure 13:
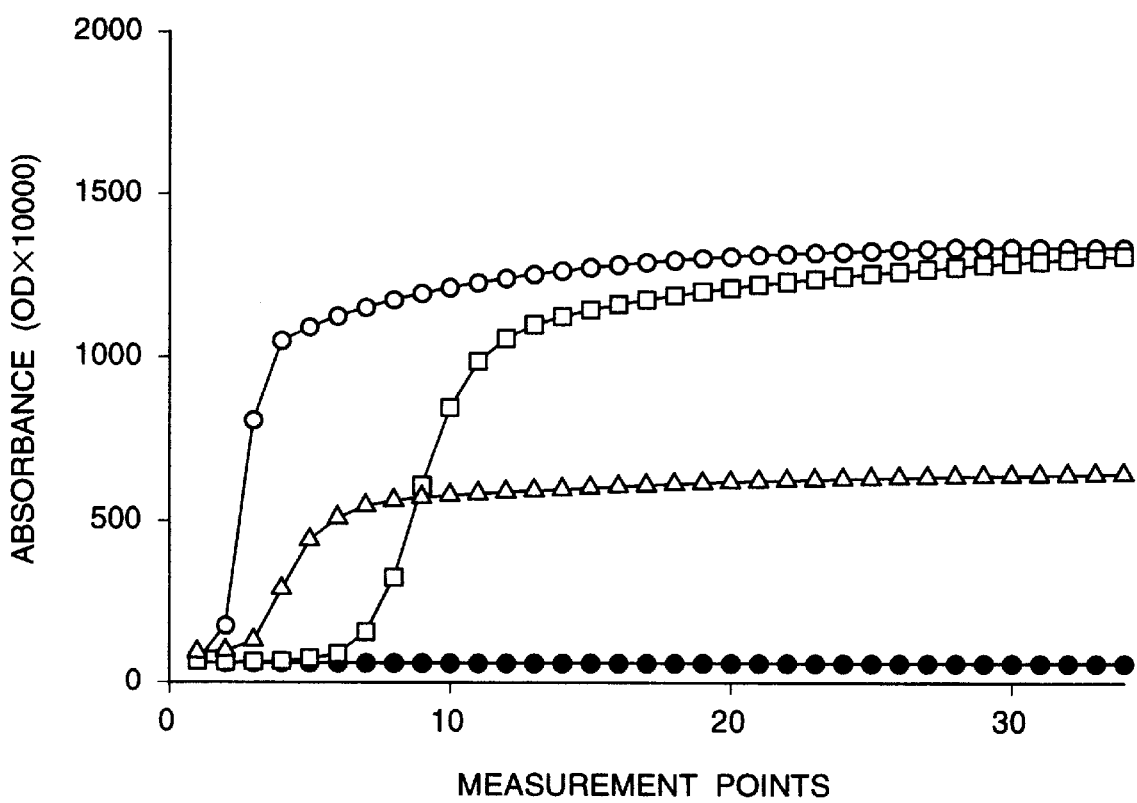
FIG. 13 is a graph showing reaction curves obtained for various lipoprotein fraction samples in Example 1 by use of reagent solution 13.

The method for measuring the amount of cholesterol in low density lipoproteins in a sample of the present invention comprises
  contacting the sample with one or more reagent solutions to carry out the reaction in the presence of a polyanion and an amphoteric surfactant, and
  subjecting the reaction product obtained above to an optical measurement to determine the amount of cholesterol.

In the above method, the optical measurement is conducted by measuring an absorbance ($OD_1$) of the solution obtained by contacting the sample with a first reagent solution, and measuring an absorbance ($OD_2$) of the solution obtained by contacting the solution for measuring $OD_1$ after measurement of $OD_1$ with a second reagent solution.

The method of the present invention is explained below with reference to the one or more reagent solutions used in the above method.

According to the present invention, the amount of cholesterol in low density lipoproteins is measured by a method comprising reacting a sample derived from a living body with ① CHE and cholesterol oxidase (hereinafter abbreviated as "CO"), or ② CHE, cholesterol dehydrogenase (hereinafter abbreviated as "CHD") and NAD(P) (nicotinamide adenine dinucleotide (phosphate)), and determining the amount of cholesterol in the sample on the basis of the amount of the produced hydrogen peroxide or NAD(P)H (reduced nicotinamide adenine dinucleotide (phosphate)), which is characterized in that a polyanion and an amphoteric surfactant are made present in the reaction system.

The present invention also provides a reagent composition for measuring the amount of cholesterol in low density lipoproteins, said reagent composition being characterized by incorporating a polyanion and an amphoteric surfactant into reagents for reacting a sample derived from a living body with ① CHE and CO, or ② CHE, CHD and NAD(P), and determining the amount of cholesterol in the sample on the basis of the amount of the produced hydrogen peroxide or NAD(P)H.

The present invention further provides a kit for measuring the amount of cholesterol in low density lipoproteins which comprises a first reagent container containing ① a polyanion and an amphoteric surfactant, ② CHE, ③ CO, peroxidase (hereinafter abbreviated as "POD") and a coupler and/or a developer, and ④ an aqueous medium, and a second reagent container containing an aqueous medium and optionally the developer or the coupler.

The present invention still further provides a kit for measuring the amount of cholesterol in low density lipoproteins which comprises a first reagent container containing ① a polyanion and an amphoteric surfactant, ② CHE, ③ CO, ④ catalase (hereinafter abbreviated as "CAT"), and ⑤ an aqueous medium, and a second reagent container containing a CAT inhibitor and an aqueous medium, wherein each of POD, a coupler and a developer is contained in at least one of the first reagent container and the second reagent container.

The present invention still further provides a kit for measuring the amount of cholesterol in low density lipoproteins which comprises a first reagent container containing ① a polyanion, ② an amphoteric surfactant, ③ CHE, ④ CHD, ⑤ NAD(P) and ⑥ an aqueous medium, and a second reagent container containing ① an aqueous medium.

In order to find a method which makes it possible to measure the amount of LDL-cholesterol directly by means of an autoanalyzer without a pretreatment for separating LDL from unnecessary lipoproteins other than LDL, the present inventors earnestly investigated and consequently found that when the amount of cholesterol in a sample derived from a living body is measured in the presence of a polyanion and an amphoteric surfactant, the cholesterol in lipoproteins other than LDL can be eliminated (consumed) by carrying out its reaction before the reaction of LDL-cholesterol by inhibiting (in other words, retarding or temporarily stopping) only the reaction of LDL-cholesterol, so that the amount of the cholesterol in LDL can be specifically measured without separating unnecessary lipoproteins other than LDL. Thus, the present invention has been accomplished.

As a method for measuring the amount of cholesterol in a sample derived from a living body, there can be exemplified methods wherein, in principle, cholesterol in the sample is reacted with CHE to be decomposed into free cholesterol and fatty acids, after which ① CO is reacted with the free cholesterol and the produced hydrogen peroxide is measured, or ② CHD and NAD(P) are reacted with the free cholesterol and the produced NAD(P)H is measured. More specifically, there can be exemplified the following methods utilizing enzyme reactions: (1) an oxidative color producing method comprising, for example, decomposing cholesterol esters in a sample derived from a living body into free cholesterol and fatty acids by use of CHE, oxidizing this free cholesterol together with free cholesterol present from the beginning into cholest-4-en-3-on and hydrogen peroxide by use of CO, carrying out an oxidative color producing reaction of an oxidizable color producing reagent (e.g. a combination of a coupler and a developer, or a color producing agent capable of producing a color by itself on oxidation) with the produced hydrogen peroxide, and colorimetrically determining the amount of the resulting oxidized dye, and (2) an ultraviolet measuring method comprising, for example, decomposing cholesterol in a sample derived from a living body into free cholesterol and fatty acids by use of CHE, reacting this free cholesterol together with free cholesterol present from the beginning with NAD(P) in the presence of CHD, and measuring the amount of the resulting NAD(P)H at 340 nm.

The method of the present invention is applicable to either of these methods. That is, according to the present invention, it is sufficient that a polyanion and an amphoteric surfactant are made present in the reaction system in practicing any of the above-exemplified methods. More specifically, a sample derived from a living body is contacted with the polyanion and the amphoteric surfactant at first to inhibit (namely, retard or temporarily stop) the reaction of LDL-cholesterol in the sample. Thus, the reaction of LDL-cholesterol is preceded by the reaction of the cholesterol in lipoproteins other than LDL to eliminate or consume this cholesterol. Then, only the amount of the above-mentioned product produced by the reaction of LDL-cholesterol is measured.

Specific examples of measuring means according to the method of the present invention are as follow.

Method 1

In the presence of a polyanion and an amphoteric surfactant, CHE and CO are acted on a sample derived from a living body to produce hydrogen peroxide, and POD and an oxidizable color producing agent (e.g. a combination of a coupler and a developer, or a color producing agent capable of producing a color by itself on oxidation) are acted on the produced hydrogen peroxide to give an oxidized dye. Absorbances in two different periods, respectively, are measured, and the amount of LDL-cholesterol in the sample is calculated on the basis of the absorbances.

Method 2

In the presence of a polyanion and an amphoteric surfactant, CHE, CHD and NAD(P) are acted on a sample derived from a living body to produce NAD(P)H, after which absorbances in two different periods, respectively, are measured, and the amount of LDL-cholesterol in the sample is calculated on the basis of the absorbances.

Method 3

In the presence of a polyanion and an amphoteric surfactant, CHE and CO are acted on a sample derived from a living body to produce hydrogen peroxide, and a combination of POD and a coupler (or a developer), or CAT is acted on the produced hydrogen peroxide and, if necessary, absorbance is measured. Then, a developer (or a coupler) or a combination of a CAT inhibitor and an oxidizable color producing reagent is acted thereon to give an oxidized dye, after which absorbance is measured and the amount of LDL-cholesterol in the sample is calculated on the basis of the absorbance(s).

Method 4

In the presence of a polyanion and an amphoteric surfactant, a combination of CHE, CHD and NAD(P), or a combination of CHE, CO, POD and a coupler and/or a developer is acted on a sample derived from a living body, to introduce the sample into a reaction system for producing NAD(P)H (or hydrogen peroxide) and, if necessary, absorbance is measured. Then, a combination of CO, POD, an oxidizable color producing reagent and a CHD inhibitor, or a combination of CHD, NAD(P) and a CO inhibitor is acted thereon to produce an oxidized dye (or NAD(P)H). Absorbance is measured and the amount of LDL-cholesterol in the sample is calculated on the basis of the absorbance(s).

In each of the above Methods 1 and 2, specifically, the two different periods are as follows: a period after substantial completion of the reaction of the cholesterol in lipoproteins other than LDL and before the initiation of the reaction of LDL-cholesterol; and a period after substantial completion of the reaction of LDL-cholesterol.

In each of the above Methods 3 and 4, although the amount of LDL-cholesterol in a sample derived from a living body can be measured by measuring absorbance in only one period, i.e., a period after substantial completion of the reaction of LDL-cholesterol, the same measurement of absorbances in two different periods, respectively, as in the above Methods 1 and 2 is preferable for further increasing the precision of measurement.

The two different periods are varied depending on the measuring method, the kinds and using concentrations of the polyanion and the amphoteric surfactant, the kinds and using concentrations of other reagents (e.g. enzymes), etc., and hence may be properly determined by investigating, for example, the reactivity (e.g. reaction curve) for each lipoprotein fraction.

The method of the present invention may be any of a one-reagent method, a two-reagent method or a method using three or more reagent solutions. However, for practical purposes, each of the above Methods 3 and 4 is preferably a two-reagent method or a method using three or more reagent solutions.

In the method using three or more reagent solutions, it is preferable that a polyanion and an amphoteric surfactant are incorporated into a reagent solution which is directly mixed with a sample derived from a living body. In each of the above Methods 1, 2 and 4, it is preferable that a combination of POD and a coupler and/or a developer, or NAD(P) is incorporated into a reagent solution which is added before initiation of the reaction of LDL-cholesterol. In the above Method 3, it is preferable that a combination of POD and a coupler, a combination of POD and a developer, or CAT is incorporated into a reagent solution which is added before initiation of the reaction of LDL-cholesterol.

Specific examples of practicing the method of the present invention as a two-reagent method are as follows.

For example, when the above Method 1 or 2 is practiced, a sample derived from a living body is mixed with a first reagent solution comprising ① a polyanion and an amphoteric surfactant, ② CHE, ③ a combination of CO, POD and an oxidizable color producing reagent, or a combination of CHD and NAD(P), and ④ an aqueous medium, after which an absorbance ($OD_1$) is measured. Then, the mixture is mixed with a second reagent solution comprising an aqueous medium, after which an absorbance ($OD_2$) is measured. On the basis of these absorbances, the amount of LDL-cholesterol in the sample is calculated.

For example, when the above Method 3 is practiced, a sample derived from a living body is mixed with a first reagent solution comprising ① a polyanion and an amphoteric surfactant, ② CHE, ③ CO, ④ POD and a coupler (or a developer) (or ④ CAT), and ⑤ an aqueous medium, after which an absorbance ($OD_1$) is measured. Then, the mixture is mixed with a second reagent solution comprising ① a developer (or a coupler) (or ① a CAT inhibitor) and ② an aqueous medium, after which an absorbance ($OD_2$) is measured. On the basis of these absorbances, the amount of LDL-cholesterol in the sample is calculated. When CAT is incorporated into the first reagent solution, each of POD, a coupler and a developer is incorporated into at least one of the first reagent solution and the second reagent solution.

For example, when the above method 4 is practiced, a sample derived from a living body is mixed with a first reagent solution comprising ① a polyanion and an amphoteric surfactant, ② CHE, ③ CHD and NAD (P) (or ③ CO, POD, and a coupler and/or a developer) and ④ an aqueous medium, after which an absorbance ($OD_1$) is measured. Then, the mixture is mixed with a second reagent solution comprising ① an aqueous medium and ② CO, POD, an oxidizable color producing reagent and a CHD inhibitor (or ② CHD, NAD(P) and a CO inhibitor), after which an absorbance ($OD_2$) is measured. On the basis of these absorbances, the amount of LDL-cholesterol in the sample is calculated.

In each of the above methods, the periods of measuring each of $OD_1$ and $OD_2$ are varied depending on the measuring method, the kinds and using concentrations of the polyanion and the amphoteric surfactant, the kinds and using concentrations of other reagents (e.g. enzymes), etc., and hence may be properly determined by investigating, for example, the reactivity (e.g. reaction curve) for each lipoprotein fraction.

When the method of the present invention is practiced as a one-reagent method in the case of the above Method 1 or 2, a more specific example of the practice is as follows.

For example, a sample derived from a living body is mixed with a reagent solution comprising ① a polyanion and an amphoteric surfactant, ② CHE, ③ a combination of CO, POD and an oxidizable color producing reagent, or a combination of CHD and NAD(P), and ④ an aqueous medium, and an absorbance ($OD_1$) is measured in a period after substantial completion of the reaction of the cholesterol in lipoproteins other than LDL and before the initiation of the reaction of LDL-cholesterol. Then, an absorbance ($OD_2$) is measured in a period after substantial completion of the reaction of LDL-cholesterol. On the basis of these absorbances, the amount of LDL-cholesterol in the sample is calculated.

In each of the above methods, the amount of LDL-cholesterol in the sample is calculated on the basis of $OD_1$ and $OD_2$ as follows: an absorbance ($OD_3$) is calculated by subtracting $OD_1$ [or a value derived from $OD_1$ (e.g. a value obtained by multiplying $OD_1$ by a correction factor for volume)] from $OD_2$, and the amount of LDL-cholesterol in the sample is determined on the basis of the thus obtained $OD_3$ value by use of a calibration curve showing the relationship between LDL-cholesterol concentration and $OD_3$ which has been previously obtained by carrying out the same measurement as described above except for using standard preparations such as standard solutions containing known concentrations of LDL-cholesterol, as samples.

In the present invention, a nonionic surfactant, an anionic surfactant, etc. may be added for accelerating the cholesterol reaction. An antibody capable of binding to lipoproteins other than LDL may also be added for accelerating the reaction of the cholesterol in lipoproteins other than LDL.

Preferable properties of the constituents used in the present invention and their using concentrations and the like are explained below.

As the polyanion used in the present invention, any polyanion may be used so long as the reaction of the cholesterol in lipoproteins other than LDL can be carried out before the reaction of LDL-cholesterol by inhibiting this reaction by making the polyanion present together with the amphoteric surfactant.

The word "inhibiting" used herein means "retarding the reaction of LDL-cholesterol as compared with the reaction of the cholesterol in lipoproteins other than LDL, or temporarily stopping the reaction of LDL-cholesterol". The word "inhibit" is used in this sence also hereinafter.

Specific examples of the polyanion are heparin, phosphotungstic acid, dextran sulfate, sulfated cyclodextrin, heparan sulfate, chondroitin sulfate, hyaluronic acid, sulfated oligosaccharides, sulfated polyacrylamides, carboxymethylated polyacrylamides, salts thereof, etc. The salts include alkali metals salts (e.g. Na salts, K salts, etc.), ammonium salts, etc.

Of the above-exemplified polyanions, heparin, phosphotungstic acid, dextran sulfate, and salts thereof are preferable. The using concentration of the polyanion may be any concentration at which the presence of the polyanion together with the amphoteric surfactant inhibits the reaction of LDL-cholesterol to precede the reaction of the cholesterol in lipoproteins other than LDL. The concentration of the polyanion in a reagent solution which is directly mixed with a sample derived from a living body is usually 0.0001% to 10% (w/v), preferably 0.001% to 1% (w/v). The above-exemplified polyanions may be used singly or in proper combination.

As the amphoteric surfactant used in the present invention, any amphoteric surfactant may be used so long as the presence of the amphoteric surfactant together with the polyanion inhibits the reaction of LDL-cholesterol to precede the reaction of the cholesterol in lipoproteins other than LDL. The amphoteric surfactant includes, for example, betaine derivatives such as alkyl betaine derivatives (e.g. lauryl betaine, stearyl betaine, lauryldimethylammonium betaine, coconut betaine, coconut oil fatty acid amidopropyl betaine, lauric acid amidopropyl betaine, etc.), imidazolinium betaine derivatives (e.g. 2-alkyl-N-carboxymethyl-N-hydroxyethyl imidazolinium betaines such as 2-lauryl-N-carboxymethyl-N-hydroxyethyl-imidazolinium betaine, 2-undecyl-N-carboxymethyl-N-hydroxyethylimidazolinium betaine, etc.; 2-alkyl-N-carboxyethyl-N-hydroxyethylimidazolium betaines, etc.), sulfobetaine derivatives (e.g. N-octyl-N,N-dimethyl-3-ammonio-1-propanesulfonic acid, N-decyl-N,N-dimethyl-3-ammonio-1-propanesulfonic acid, N-dodecyl-N,N-dimethyl-3-ammonio-1-propanesulfonic acid, N-tetradecyl-N,N-dimethyl-3-ammonio-1-propanesulfonic acid, N-hexadecyl-N,N-dimethyl-3-ammonio-1-propanesulfonic acid, etc.), aminocarboxylic acid derivatives such as alkylglycines, alkylbis-(aminoethyl)glycines, dioctylpolyaminoethyl glycines, N-alkylpolyamino-ethyl glycines, β-alanine derivatives, etc.; imidazoline derivatives such as bis(2-undecyl-N-hydroxyethylimidazoline) chloroacetic acid complex, alkylimidazoline derivatives, etc.; and amine oxide derivatives such as lauryldimethylamine oxide, etc.

Of the above-exemplified amphoteric surfactants, lauryl betaine, coconut oil fatty acid amidopropyl betaine, lauric acid amidopropyl betaine, 2-alkyl-N-carboxymethyl-N-hydroxyethylimidazolinium betaines and 2-alkyl-N-carboxy-methyl-N-hydroxyethylimidazolinium betaines are preferable.

The using concentration of the amphoteric surfactant may be any concentration at which the presence of the amphoteric surfactant together with the polyanion inhibits the reaction of LDL-cholesterol to precede the reaction of the cholesterol in lipoproteins other than LDL. The concentration of the amphoteric surfactant in a reagent solution which is directly mixed with a sample derived from a living body is usually 0.0001% to 10% (w/v), preferably 0.001% to 1% (w/v). The above-exemplified amphoteric surfactants may be used singly or in proper combination.

As the CO used in the present invention, there can be exemplified those usually used in the art, such as those derived from microorganisms belonging to genera Nocardia, Pseudomonas, etc., and those derived from animal organs such as bovine pancreas, etc. As to the using amount of CO, for example, its concentration in a first reagent solution in a two-reagent method is usually 0.03 to 330 u/ml, preferably 0.07 to 130 u/ml, more preferably 0.13 to 65 u/ml. The concentration of CO in the final reaction solution for measuring LDL-cholesterol is usually 0.02 to 250 u/ml, preferably 0.05 to 100 u/ml, more preferably 0.1 to 50 u/ml.

In a one-reagent method, the using concentration of CO is properly chosen in the above concentration range in the final reaction solution (hereinafter the same applied).

As the CHE used in the present invention, there can be exemplified those usually used in the art, such as those derived from microorganisms belonging to genera Candida, Pseudomonas, etc., and those derived from animal organs such as bovine pancreas, etc. As to the using amount of CHE, for example, its concentration in a first reagent solution in a two-reagent method is usually 0.03 to 330 u/ml, preferably 0.07 to 130 u/ml, more preferably 0.13 to 65 u/ml. The concentration of CHE in the final reaction solution for measuring LDL-cholesterol is usually 0.02 to 250 u/ml, preferably 0.05 to 100 u/ml, more preferably 0.1 to 50 u/ml.

As the POD used in the present invention, there can be exemplified those usually used in the art, such as those derived from plants (e.g. horseradish, radish, etc.), those derived from microorganisms (e.g. molds, yeasts, etc.), and those derived from leukocytes, thyroids, etc. of animals. As to the using amount of POD, for example, its concentration in a first reagent solution in a two-reagent method is usually 0.1 to 1,000 u/ml, preferably 0.25 to 400 u/ml, more preferably 0.5 to 200 u/ml. The concentration of POD in the final reaction solution for measuring LDL-cholesterol is usually 0.1 to 250 u/ml, preferably 0.25 to 100 u/ml, more preferably 0.5 to 50 u/ml.

As the oxidizable color producing reagent used in the present invention, any oxidizable color producing reagent may be used so long as it reacts with hydrogen peroxide in the presence of POD to produce a color. There can be exemplified combinations of a coupler such as 4-aminoantipyrine (hereinafter abbreviated as "4-AA") and a developer which can produce a dye on oxidative condensation with the coupler, for example, combinations of 4-AA and a phenolic compound, a naphthol compound or an aniline compound, combinations of 3-methyl-2-benzothiazolinone hydrazone and an aniline compound, etc.; and color producing agents which can produce a color by themselves on oxidation, such as 2,2'-azinobis(3-ethylbenzothiazolin-6-sulfonic acid), triphenylmethane leuco dyes, diphenylamine derivatives, benzidine derivatives, triallylimidazole derivatives, leucomethylene blue derivatives, o-phenylene-diamine derivatives, etc.

As the developer, specific examples of the phenolic compound are phenol, p-chlorophenol, 2,4-dichlorophenol, etc. Specific examples of the naphthol compound are 1-naphthol, 1-naphthol-2-sulfonic acid, 1-naphthol-2-carboxylic acid, etc. Specific examples of the aniline compound are N,N-diethylaniline, N-ethyl-N-(β-hydroxyethyl)-m-toluidine, N-ethyl-N-(2-hydroxy-3-sulfopropyl)- 3,5-dimethoxyaniline (DAOS), N-ethyl-N-(2-hydroxy-3-sulfopropyl)-3,5-dimethoxy-4-fluoroaniline (FDAOS), N-(2-hydroxy-3-sulfopropyl)-3,5-dimethoxyaniline (HDAOS), N-ethyl-N-(2-hydroxy-3-sulfopropyl)-m-toluidine (TOOS), N-ethyl-N-(3-methylphenyl)-N'-succinyl-ethylene-diamine (EMSE), etc.

When a combination of the coupler and the developer is used, the using amount of the coupler is varied depending on the kind of the coupler, the kind of the developer combined therewith, etc. For example, the concentration of the coupler in a first reagent solution in a two-reagent method is usually 0.01 to 400 mM, preferably 0.1 to 40 mM, more preferably 0.2 to 10 mM. The concentration of the coupler in the final reaction solution for measuring LDL-cholesterol is usually 0.01 to 100 mM, preferably 0.1 to 10 mM. When 4-AA is used as the coupler, its using amount is as follows: for example, the concentration of 4-AA in a first reagent solution in a two-reagent method is usually 0.01 to 200 mM, preferably 0.1 to 40 mM, more preferably 0.2 to 10 mM, and the concentration of 4-AA in the final reaction solution for measuring LDL-cholesterol is usually 0.01 to 50 mM, preferably 0.1 to 5 MM.

The using amount of the developer cannot be unequivocally determined because it is varied depending on the kind of the developer, the kind of the coupler combined therewith, etc. For example, the concentration of the developer in a first reagent solution in a two-reagent method is usually 0.01 to 200 mM, preferably 0.1 to 40 mM, more preferably 0.2 to 10 mM. The concentration of the developer in the final reaction solution for measuring LDL-cholesterol is usually 0.01 to 50 mM, preferably 0.1 to 5 mM.

Specific examples of the triphenylmethane leuco dyes are leuco-Malachite Green, bis(p-diethylaminophenyl)-2-sulfophenylmethane, bis(p-diethylaminophenyl)-3,4-disulfopropoxyphenylmethane•disodium salt, etc. Specific examples of the diphenylamine derivatives are bis[4-di(2-butoxyethyl)amino-2-methylphenyl]amine, N,N-bis(4-diethylamino-2-methylphenyl)-N'-p-toluenesulfonyl urea, etc. Specific examples of the leucomethylene blue derivatives are 10-(carboxymethylaminocarbonyl)-3,7-bis(dimethylamino)phenothiazine•sodium salt, 10-[3-(methoxycarbonylaminomethyl)phenylmethylaminocarbonyl]-3,7-bis(dimethylamino) phenothiazine, etc. Specific examples of the benzidine derivatives are benzidine, o-tolidine, o-dianisidine, 3,3'-diaminobenzidine, 3,3',5,5'-tetraaminobenzidine, etc. Specific examples of the triallylimidazole derivatives are 2-(4-carboxyphenyl)-3-N-methylcarbamoyl-4,5-bis(4-diethylaminophenyl)imidazole, 2-(3-methoxy-4-diethylaminophenyl)-3-N-methylcarbamoyl-4,5-bis(2-methyl-4-diethylaminophenyl)imidazole, etc.

The using amount of the above-exemplified color producing agents is chosen in the concentration range usually employed in the art.

As the CAT used in the present invention, there can be exemplified those usually used in the art, such as those derived from animal organs (e.g. bovine pancreas, etc.), those derived from chloroplast, etc. of plants, and those derived from microorganismes belonging to genera Micrococcus, Rhodopseudomonas, etc. As to the using amount of CAT, for example, its concentration in a first reagent solution in a two-reagent method is usually 10 to 50,000 u/ml, preferably 100 to 5,000 u/ml, more preferably 0.5 to 50 u/ml.

As the CHD used in the present invention, there can be exemplified those usually used in the art, such as those derived from bacteria of genus Nocardia. As to the using amount of CHD, for example, its concentration in a first reagent solution in a two-reagent method is usually 0.1 to 150 u/ml, preferably 0.3 to 100 u/ml, more preferably 0.5 to 60 u/ml. The concentration of CHD in the final reaction solution for measuring LDL-cholesterol is usually 0.1 to 100 u/ml, preferably 1 to 50 u/ml.

As the NAD(P) used in the present invention, there can be exemplified those usually used in the art, such as those derived from yeasts. As to the using amount of NAD(P), for example, its concentration in a first reagent solution in a two-reagent method is usually 0.2 to 70 mM, preferably 0.5 to 50 mM, more preferably 1 to 20 mM. The concentration of NAD(P) in the final reaction solution for measuring LDL-cholesterol is usually 0.2 to 50 mM, preferably 1 to 10 mM.

As the CAT inhibitor used in the present invention, there can be exemplified those usually used in the art, such as $NaN_3$, 3-amino-1,2,4-triazole, etc. The using amount of the CAT inhibitor cannot be unequivocally determined because it is varied depending on the kind of the CAT inhibitor. For example, the concentration of CAT inhibitor in a second reagent solution in a two-reagent method is usually 0.01 to 10% (w/v), preferably 0.02 to 5% (w/v), more preferably 0.03 to 3% (w/v).

As the CO inhibitor used in the present invention, there can be exemplified those usually used in the art, such as $Ag^+$ ion, $Zn^{2+}$ ion, glutathione, etc. The using amount of the CO inhibitor cannot be unequivocally determined because it is varied depending on the kind of the CO inhibitor. For example, the concentration of CO inhibitor in a second reagent solution in a two-reagent method is usually 0.00002 to 40% (w/v), preferably 0.0002 to 4% (w/v), more preferably 0.002 to 0.4% (w/v).

As the CHD inhibitor used in the present invention, there can be exemplified those usually used in the art, such as $Ag^+$ ion, $Zn^{2+}$ ion, etc. The using amount of the CHD inhibitor cannot be unequivocally determined because it is varied depending on the kind of the CHD inhibitor. For example, the concentration of CHD inhibitor in a second reagent solution in a two-reagent method is usually 0.00001 to 70% (w/v), preferably 0.0001 to 7% (w/v), more preferably 0.001 to 0.7% (w/v).

As the nonionic surfactant and the anionic surfactant which are used in the present invention, any nonionic surfactant and any anionic surfactant, respectively, may be used so long as they can accelerate the cholesterol reaction. The nonionic surfactant includes, for example, polyoxyethylene alkyl ethers, polyoxyethylene alkylphenyl ethers, polyoxyethylene higher alcohol ethers, polyoxyethylene fatty acid esters, polyoxyethylene sorbitan fatty acid esters, sorbitan fatty acid esters, polyoxyethylene sorbitol fatty acid esters, polyoxyethylene alkylamines, glycerol fatty acid esters, etc. The anionic surfactant includes, for example, cholic acid and derivatives thereof. Specific examples of the polyoxyethylene alkyl ethers are polyoxyethylene lauryl ethers, polyoxyethylene cetyl ethers, polyoxyethylene stearyl ethers, polyoxyethylene oleyl ethers, etc. Specific examples of the polyoxyethylene alkylphenyl ethers are polyoxyethylene octylphenyl ethers, polyoxyethylene nonylphenyl ethers, etc. Specific examples of the polyoxyethylene fatty acid esters are polyethylene glycol monolaurates, polyethylene glycol monostearates, polyethylene glycol distearates, polyethylene glycol monooleates, etc. Specific examples of the polyoxyethylene sorbitan fatty acid esters are polyoxyethylene sorbitan monolaurates, polyoxyethylene sorbitan monopalmitates, polyoxyethylene sorbitan monostearates, polyoxyethylene sorbitan tristearates, polyoxyethylene sorbitan monooleates, polyoxyethylene sorbitan trioleates, etc. Specific examples of the sorbitan fatty acid esters are sorbitan monolaurate, sorbitan monopalmitate, sorbitan monostearate, sorbitan distearate, sorbitan tristearate, sorbitan monooleate, sorbitan trioleate, sorbitan sesquioleate, etc. Specific examples of the polyoxyethylene sorbitol fatty acid esters are polyoxyethylene sorbite tetraoleates, etc. Specific examples of the polyoxyethylene alkylamines are polyoxyethylene laurylamine, polyoxyethylene stearylamine, etc. Specific examples of the glycerol fatty acid esters are stearic acid monoglyceride, oleic acid monoglyceride, etc.

Specific examples of the anionic surfactant are cholic acid, deoxycholic acid, polyoxyethylene alkylphenol ether sulfates, dodecylbenzenesulfonates, lauroylsarcosine, etc.

The using concentration of the surfactants exemplified above is as follows. When the nonionic surfactant is used singly in a one-reagent method, their concentration in the reagent solution is usually 0.0001% to 10% (w/v), preferably 0.001% to 1% (w/v). When the nonionic surfactant is used singly in a two-reagent method, their concentration in a first reagent solution is usually 0.0001% to 5% (w/v), preferably 0.001% to 0.5% (w/v), and their concentration in a second reagent solution is usually 0.01 to 20% (w/v), preferably 0.05 to 5% (w/v), though the concentrations are varied depending on the volume ratio of the first reagent solution to the second reagent solution, etc.

When the anionic surfactant is used singly in a one-reagent method, their concentration in the reagent solution is usually 0.0001% to 10% (w/v), preferably 0.001% to 1% (w/v). When the anionic surfactant is used singly in a two-reagent method, their concentration in a first reagent solution is usually 0.0001% to 5% (w/v), preferably 0.001% to 0.5% (w/v), and their concentration in a second reagent solution is usually 0.01 to 20% (w/v), preferably 0.05 to 5% (w/v), though the concentrations are varied depending on the volume ratio of the first reagent solution to the second reagent solution, etc.

When the nonionic surfactant and the anionic surfactant are used in combination in a one-reagent method, their concentration in the reagent solution is usually 0.0001% to 20% (w/v), preferably 0.001% to 2% (w/v). When the nonionic surfactant and the anionic surfactant are used in combination in a two-reagent method, their total concentration in a first reagent solution is usually 0.0001% to 10% (w/v), preferably 0.001% to 1% (w/v), and their total concentration in a second reagent solution is usually 0.01 to 40% (w/v), preferably 0.05 to 10% (w/v), though the concentrations are varied depending on the volume ratio of the first reagent solution to the second reagent solution, etc.

The above-exemplified surfactants may be used singly or as a mixture thereof.

As the antibody capable of binding to lipoproteins other than LDL which is used in the present invention, any antibody may be used so long as it can accelerate the reaction of the cholesterol in lipoproteins other than LDL. There can be exemplified anti-HDL antibody, anti-apolipoprotein A antibody, anti-apolipoprotein C antibody, anti-apolipoprotein E antibody, anti-α-lipoprotein antibody, anti-VLDL antibody, anti-preβ-lipoprotein antibody, etc. These antibodies may be either polyclonal antibodies or monoclonal antibodies and may be used singly or in combination.

The antibody capable of binding to lipoproteins other than LDL also includes fragments [e.g. Fab, Fab', F(ab')$_2$, etc.] obtained by enzymatic or chemical decomposition of the above-exemplified antibody, enzyme-modified antibodies obtained by labeling the above-exemplified antibody with an enzyme, etc.

In the present invention, it is preferable to use a modified antibody endowed with or improved in an ability to accelerate the reaction of the cholesterol in lipoproteins other than LDL, which is obtained by bonding a suitable compound to the above-exemplified antibody.

The compound may be either a natural compound or a chemical synthetic compound. It includes, for example, sugars, fatty acids, various glycosides (e.g. alkaloid glycosides, steroid glycosides, terpenoid glycosides, etc.), water-soluble synthetic polymers, etc. Any of these compounds can easily be bonded to the antibody by covalently bonding the amino group, imino group, carboxyl group, aldehyde group or 2,3-epoxypropyl group of the compound to the amino group, carboxyl group or sulfhydryl group of the antibody by a conventional method. When the compound had no active group for the modification, it can easily be bonded to the antibody by a method of activating the compound and then carrying out the modification, or a method of carrying out the modification through a cross-linking agent.

Specific examples of the compound are dextran, pullulan, Ficoll, dextrin, cyclodextrin, poly(glutamic acid)s, poly (aspartic acid)s, pectic acid, protuberic acid, alginic acid, carboxymethyldextran, carboxymethyl cellulose, polylysines, albumin, laminaran, lichenan, lectin, dextran sulfate, chondroitin sulfate, heparin, glucose, galactose, xylose, fructose, lactose, maltose, palatinose, trehalose, mannose, fucose, glucuronic acid, glucosamine, galactosamine, inositol, sialic acid, muramic acid, glycyrrhetinic acid, arbutin, daidzin, poly(vinyl alcohol)s, poly(ethylene glycol)s, poly(vinylpyrrolidone)s, etc.

Of the compounds exemplified above, compounds having an active group (e.g. amino group, carboxyl group, imino group, aldehyde group, sulfhydryl group, etc.) for the amino group, carboxyl group or sulfhydryl group of the antibody may be subjected as they are to bonding reaction with the antibody. Compounds having no active group may be used after being activated according to any of the following methods for introducing an active group. The active group may be introduced through a spacer having a suitable molecular length, such as an alkylene group having 1 to 6 carbon atoms.

The methods for introducing an active group into the above-exemplified compound are, for example, following conventional introduction methods: a method for introducing an active group by use of cyanuric chloride [e.g. J. Solid-phase Biochem., Vol. 4, 2128 (1976)], a method for introducing an aldehyde group by use of metaperiodic acid [e.g. Proc. Nati. Acad. Sci. USA., Vol. 73, 2128 (1976)], a method for introducing an imino group by use of cyanogen bromide [e.g. Nature, Vol. 214, 1302 (1967)], a method for introducing a 2,3-epoxypropyl group by use of epichlorohydrin [e.g. J. Chromatog. Vol. 51, 479 (1970)], a method for introducing a carboxyl group by use of a carboxylic anhydride (e.g. JP-A 5-268950), a method for introducing a carboxyl group by use of a monobromocarboxylic acid [e.g. Arc. Biochem. Biophys., Vol. 147, 788 (1971)], etc., these references being incorporated herein by reference.

As a method for covalently bonding a compound having an active group to the antibody, all conventional bonding methods can be exemplified. For example, when the mutually reactive groups which participate in the reaction are an amino group and a carboxyl group, there can be exemplified a carbodiimide method [e.g. J. Biol. Chem., Vol. 245, 3059 (1970)], an activated ester method [e.g. Cancer Biochem., Vol. 7, 175 (1984)], an acid anhydride method [e.g. J. Biol. Chem., Vol. 237, 1825 (1962)], an azide method [e.g. Eur. J. Biochem., Vol. 25, 129 (1972)], an acid chloride method [e.g. Angew. Chem., Vol. 67, 661 (1955)], an isocyanate method [e.g. Nature, Vol. 210, 367 (1966)], a Woodward reagent method [e.g. Biochim. Biophys. Acta, Vol. 178, 626 (1969)], Ugi reaction [e.g. Angew. Chem., Vol. 74, 9 (1962)], etc. When the mutually reactive groups are amino groups, there can be exemplified a glutaraldehyde method [e.g. Experientia, Vol. 28, 958 (1973)], an alkylation method [e.g. Biochim., Biophys. Acta, Vol. 198, 276 (1970)], etc., these references being incorporated herein by reference. When the mutually reactive groups are a hydroxyl group and an amino group, there can be exemplified the alkylation method [e.g. Biochim., Biophys. Acta, Vol. 198, 276 (1970)], etc., this reference being incorporated by reference. When the mutually reactive groups are amino group and an aldehyde group, there can be exemplified a periodate oxidation method [e.g. Proc. Natl. Acad. Sci. USA, Vol. 73, 2128 (1978)], etc., this reference being incorporated herein by reference. When the mutually reactive groups are an amino group and an imino group, there can be exemplified the cyanogen bromide method [e.g. Nature, Vol. 214, 1302 (1967)], etc., this reference being incorporated herein by reference.

The using concentration of the above-mentioned antibody may be any concentration at which the reaction of the cholesterol in lipoproteins other than LDL can be accelerated. The concentration of the antibody in a reagent which is directly mixed with a sample derived from a living body is usually 0.001 to 10 mgAb/ml, preferably 0.01 to 1 mgAb/ml.

The aqueous medium used in the present invention includes water, buffer solutions, etc. As the buffer, any buffer may be used so long as it has buffer action in a pH range of 5 to 11 and does not inhibit the reactions for cholesterol measurement. There can be exemplified buffers usually used in the art, such as tris(hydroxymethyl)-aminomethane, Good's buffers, phosphoric acid salt, boric acid salt, etc. The using concentration of the buffer is usually 1 mM to 2 M, preferably 10 mM to 1 M. The pH of the buffer solution is usually 5 to 11, preferably 6 to 8, more preferably about 7.

The reagent, reagent composition and kit for measuring the amount of LDL-cholesterol of the present invention are used for measuring the amount of LDL-cholesterol in a sample derived from a living body, such as serum, plasma or the like. It is sufficient that each of the reagent, the reagent composition and the kit is prepared so as to contain, besides the polyanion and the amphoteric surfactant, the above-mentioned reagents used in a method for measuring the amount of cholesterol in a sample derived from a living body, such as CO, CHE, CHD, POD, NAD(P), the oxidizable color producing reagent, CAT, the CAT inhibitor, CO inhibitor, CHD inhibitor, the aqueous medium, and optionally the nonionic surfactant, the anionic surfactant, the antibody, etc. in concentration ranges usually employed in the art. Preferable properties and the using concentrations of the constituents are as described above. If necessary, said kit may be accompanied with LDL-cholesterol standard preparations, etc. As the standard preparations, for example, standard sera prepared from human or animal serum and standard solution contained LDL fraction may be used as the standard preparations.

In the case of the method, reagent, reagent composition and kit for measuring the amount of LDL-cholesterol of the present invention, the reaction of LDL-cholesterol is inhibited by the presence of the polyanion and the amphoteric surfactant to precede the reaction of the cholesterol in lipoproteins other than LDL. Then, the reaction of LDL-cholesterol is allowed to proceed, followed by specific measurement of only hydrogen peroxide or NAD(P)H, which is produced by the reaction of LDL-cholesterol. Therefore, the method, the reagent, the reagent composition and the kit make it possible to measure LDL-cholesterol by an end point assay using a conventional autoanalyzer which has been difficult to carry out by a conventional method.

Preferable embodiments of the present invention are, for example, as follows.

A sample derived from a living body, such as serum, plasma or the like is mixed with a first reagent solution containing ① a polyanion and an amphoteric surfactant, ② CHE, ③ a combination of CO, a developer, a coupler and POD, or a combination of CHD and NAD(P), and ④ a buffer and optionally a nonionic surfactant and/or an anionic surfactant, an antibody, etc. The reaction is carried out at 2° C. to 40° C. for 1 to 30 minutes, after which an absorbance ($OD_1$) is measured. Then, the reaction solution is mixed with a second reagent solution containing a buffer and optionally a nonionic surfactant and/or an anionic surfactant, and the reaction is carried out at 2° C. to 40° C. for 1 to 60 minutes, after which an absorbance ($OD_2$) is measured. An absorbance ($OD_3$) is calculated by subtracting a value derived from $OD_1$ (e.g. a value obtained by multiplying $OD_1$ by a correction factor for volume) from $OD_2$, and the amount of LDL-cholesterol in the sample is determined on the basis of the thus obtained $OD_3$ value by use of a calibration curve showing the relationship between LDL-cholesterol concentration and $OD_3$ which has been previously obtained by carrying out the same measurement as described above except for using standard preparations such as standard solutions containing known concentrations of LDL-cholesterol, as samples.

Further, a sample derived from a living body, such as serum, plasma or the like is mixed with a first reagent solution containing ① a polyanion and an amphoteric surfactant, ② CHE, ③ CO, a developer (or a coupler) and POD, and ④ a buffer and optionally a nonionic surfactant and/or an anionic surfactant, an antibody, etc. The reaction is carried out at 2° C. to 40° C. for 1 to 30 minutes, after which an absorbance ($OD_1$) is measured. Then, the reaction solution is mixed with a second reagent solution containing a coupler (or a developer), a buffer and optionally a nonionic surfactant and/or an anionic surfactant, and the reaction is carried out at 2° C. to 40° C. for 1 to 60 minutes, after which an absorbance ($OD_2$) is measured. An absorbance ($OD_3$) is calculated by subtracting a value derived from $OD_1$ (e.g. a value obtained by multiplying $OD_1$ by a correction factor for volume) from $OD_2$, and the amount of LDL-cholesterol in the sample is determined on the basis of the thus obtained $OD_3$ value by use of a calibration curve showing the relationship between LDL-cholesterol concentration and $OD_3$ which has been previously obtained by carrying out the same measurement as described above except for using standard preparations such as standard solutions containing known concentrations of LDL-cholesterol, as samples.

Still further, a sample derived from a living body, such as serum, plasma or the like is mixed with a first reagent solution containing ① a polyanion and an amphoteric surfactant, ② CHE, ③ CO, a developer (or a coupler), ④ CAT, and ⑤ a buffer and optionally a nonionic surfactant and/or an anionic surfactant, an antibody, etc. The reaction is carried out at 2° C. to 40° C. for 1 to 30 minutes, after which an absorbance ($OD_1$) is measured. Then, the reaction solution is mixed with a second reagent solution containing a coupler (or a developer), POD, a CAT inhibitor, a buffer and optionally a nonionic surfactant and/or an anionic surfactant, and the reaction is carried out at 2° C. to 40° C. for 1 to 60 minutes, after which an absorbance ($OD_2$) is measured. An absorbance ($OD_3$) is calculated by subtracting a value derived from $OD_1$ (e.g. a value obtained by multiplying $OD_1$ by a correction factor for volume) from $OD_2$, and the amount of LDL-cholesterol in the sample is determined on the basis of the thus obtained $OD_3$ value by use of a calibration curve showing the relationship between LDL-cholesterol concentration and $OD_3$ which has been previously obtained by carrying out the same measurement as described above except for using standard preparations such as standard solutions containing known concentrations of LDL-cholesterol, as samples.

In the case of a one-reagent method, a sample derived from a living body, such as serum, plasma or the like is mixed with a reagent solution containing ① a polyanion and an amphoteric surfactant, ② CHE, ③ a combination of CO, POD and an oxidizable color producing reagent, or a combination of CHD and NAD(P), and ④ a buffer and optionally a nonionic surfactant and/or an anionic surfactant, an antibody, etc. The reaction is carried out at 2° C. to 40° C. for 1 to 30 minutes, after which an absorbance ($OD_1'$) is measured. Then, the reaction is continued at 2° C. to 40° C. for 1 to 60 minutes, after which an absorbance ($OD_2'$) is measured. An absorbance ($OD_3'$) is calculated by subtracting $OD_1'$ from $OD_2'$, and the amount of LDL-cholesterol in the sample is determined on the basis of the thus obtained $OD_3'$ value by use of a calibration curve showing the relationship between LDL-cholesterol concentration and $OD_3'$ which has been previously obtained by carrying out the same measurement as described above except for using standard preparations such as standard solutions containing known concentrations of LDL-cholesterol, as samples.

In the above embodiments, as the periods in which $OD_1$ (or $OD_1'$) and $OD_2$ (or $OD_2'$), respectively, are measured, the most suitable periods may be properly chosen in the above-mentioned ranges by investigating the reactivity (e.g. reaction curve) for each lipoprotein fraction.

The present invention is illustrated below in further detail with reference to Examples and Reference Examples, which are not by way of limitation but by way of illustration.

EXAMPLE 1

Reaction curves of reagent compositions of the present invention with various lipoproteins fractionated by ultracentrifugation were measured by using Autoanalyzer Hitachi 7170 (mfd. by Hitachi Ltd.).

Samples

As samples, there were used a HDL fraction (cholesterol: 84 mg/dl), a LDL fraction (cholesterol: 95 mg/dl) and a VLDL fraction (cholesterol: 33 mg/dl) which had been prepared by fractionation from serum by a conventional ultracentrifugation method.

Reagents

Reagent Solutions 1 to 13

As reagent solutions, there were used 25 mM 2-hydroxy-N-tris(hydroxymethyl)methyl-3-aminopropanesulfonic acid (TAPSO)-NaOH buffer solutions (pH 7.0) containing 1 U/ml of CO (serial number COO-321, available from TOYOBO Co., Ltd.), 1 U/ml of CHE (serial number T-18, available from Asahi Kasei Kogyo K.K.), 0.5 MM of N-(2-hydroxy-3-sulfopropyl)-3,5-dimethoxyaniline (HDAOS), 1 mM of 4-AA, 1.5 U/ml of POD (serial number PEO-302, available from TOYOBO Co., Ltd.), 0.04% (w/v) of a predetermined polyanion and 0.008% (w/v) of a predetermined amphoteric surfactant.

Table 1 shows the specific names of the polyanion and the amphoteric surfactant which were used in each reagent solution.

TABLE 1

| Reagent solution | Amphoteric surfactant | Polyanion |
|---|---|---|
| Reagent solution 1 | None | None |
| Reagent solution 2 | LEBON 50 (a trade name, Sanyo Chemical Industries, Ltd.) (alkylpolyamino-ethyl glycine hydrochloride) | Heparin |
| Reagent solution 3 | CLINK PA-12 (a trade name, YOSHIMURA OIL CHEMICAL CO., LTD.) (N-laurylamino-propionate) | Heparin |
| Reagent solution 4 | AMOGEN K (a trade name, DAI-ICHI KOGYO SEIYAKU CO., LTD.) (N,N,N-trialkyl-N-carboxymethyl) | Heparin |

TABLE 1-continued

| Reagent solution | Amphoteric surfactant | Polyanion |
|---|---|---|
| Reagent solution 5 | AMPHITOL 24B (a trade name, Kao Corporation) (lauryl betaine) | Heparin |
| Reagent solution 6 | ENAGICOL C40H (LION CORPORATION) (2-alkyl-N-carboxyalkyl-N-hydroxyethyl imidazolinium betaine) | Heparin |
| Reagent solution 7 | LEBON 15 (a trade name, Sanyo Chemical Industries, Ltd.) (alkylpolyamino-ethyl glycine hydrochloride) | Phosphotungstic acid |
| Reagent solution 8 | SALABON 50 (a trade name, TAKEMOTO OIL & FATS CO., LTD.) (a mixture of monooctylaminoethylglycine hydrochloride and dioctylaminoethylglycine hydrochloride) | Phosphotungstic acid |
| Reagent solution 9 | AMOGEN K | Phosphotungstic acid |
| Reagent solution 10 | NISSAN ANON LG (a trade name, NIPPON OIL & FATS CO., LTD.) [alkyldi(aminoethyl) glycine] | Phosphotungstic acid |
| Reagent solution 11 | AMPHITOL 24B | Phosphotungstic acid |
| Reagent solution 12 | ENAGICOL C40H | Phosphotungstic acid |
| Reagent solution 13 | LEBON LAG40 (a trade name, Sanyo Chemical Industries, Ltd.) (alkyl-diamino-ethyl glycine hydrochloride) | Phosphotungstic acid |

Measuring Conditions

LDL-cholesterol was measured by setting measuring as follow:

Measuring method: 1 Point end [34]-[0]

Volume of sample: 2.5 $\mu$l

Volume of reagent solution: 300 $\mu$l

Measuring wavelength: 700/600 nm

Measuring temperature: 37° C.

Results

FIGS. 1 to 13 show the measurement results obtained by use of reagent solutions 1 to 13, respectively.

In FIGS. 1 to 13, -□- shows the results obtained for the LDL fraction sample, -○- the results obtained for the HDL fraction sample, -△- the results obtained for the VLDL fraction sample, and -●- the results obtained by using physiological saline as a sample.

As is clear from the results shown in FIG. 1, immediately after mixing of each sample with the reagent solution containing neither polyanion nor amphoteric surfactant (reagent solution 1), the reaction of the reagent solution with each of LDL, HDL and VLDL begins, and it substantially reaches a plateau in 2 to 5 minutes.

On the other hand, as can be seen from FIGS. 2 to 13, when cholesterol in lipoproteins is measured in the presence of a polyanion and an amphoteric surfactant (reagent solutions 2 to 13), the reaction with LDL is inhibited, namely, the reaction with LDL still proceeds inspite of substantial completion of the reactions with HDL and VLDL, respectively (in the case of reagent solutions 2 and 3), or the reaction with LDL begins after substantial completion of the reactions with HDL and VLDL, respectively (in the case of reagent solutions 4 to 13).

From the above, it can be seen that the presence of a polyanion and an amphoteric surfactant makes it possible to allow the reaction of LDL-cholesterol to proceed after retarding or temporarily stopping this reaction to precede the reaction of the cholesterol in lipoproteins other than LDL, namely, the presence permits specific measurement of LDL-cholesterol.

EXAMPLE 2

The amount of LDL-cholesterol in serum was measured by the measuring method of the present invention by using Autoanalyzer Hitachi 7170 (mfd. by Hitachi Ltd.).

Samples

Ten fresh sera.

Reagent

Reagent Solution 14

R-1: 25 mM TAPSO-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Triton X-100, 1 mM of 4-AA and 10 U/ml of POD (serial number PEO-302, available from TOYOBO Co., Ltd.).

R-2: 25 mM TAPSO-NaOH buffer (pH 7.0) containing 0.5% (w/v) of Emalgen 709 (a polyoxyethylene higher alcohol ether, a trade name, Kao Corporation).

Measuring Conditions

The measurement was carried out by setting measuring parameters as follow:

Measuring method: 2 Point end [16]-[34]

Volume of sample: 3 $\mu$l

Volume of R-1: 270 $\mu$l

Volume of R-2: 90 $\mu$l

Measuring wavelength: 700/600 nm

Measuring temperature: 37° C.

Results

The results obtained are shown in Table 2.

REFERENCE EXAMPLE 1

The LDL-cholesterol value in each of the same sera as used in Example 2 was calculated according to the Friedewald equation, a conventional method.

The measuring procedure was carried out according to CLINICAL CHEMISTRY. Vol. 18, No. 6, p.499–502 (1972).

Results

The measurement results are also shown in Table 2.

TABLE 2

| Sample No. | Example 2 (Reagent solution 14) (mg/dl) | Friedewald calculated value (mg/dl) |
|---|---|---|
| 1 | 127.5 | 125.5 |
| 2 | 96.9 | 97.2 |
| 3 | 169.3 | 171.1 |
| 4 | 131.8 | 129.9 |

TABLE 2-continued

| Sample No. | Example 2 (Reagent solution 14) (mg/dl) | Friedewald calculated value (mg/dl) |
|---|---|---|
| 5 | 104.0 | 100.4 |
| 6 | 138.9 | 140.3 |
| 7 | 134.5 | 125.8 |
| 8 | 141.5 | 140.3 |
| 9 | 134.5 | 132.4 |
| 10 | 141.6 | 135.3 |
| Mean value | 132.1 | 129.8 |
| Coefficient of correlation with Reference Example 1 | 0.99 | — |
| Inclination of regression line | 0.96 | — |
| y Intercept of regression line | 8.05 | — |

As is clear from the results shown in Table 2, the cholesterol values obtained by use of the reagent containing a polyanion and an amphoteric surfactant of the present invention (reagent solution 14) are in good correlation with the cholesterol values obtained according to the Friedewald equation, a conventional method, namely, LDL-cholesterol can be specifically measured using said reagent.

EXAMPLE 3

The amount of LDL-cholesterol in control sera [available from PBI (Pacific Biometrics, Inc.)] each having a known LDL-cholesterol value measured by BQ method (Beta quantification method) was measured by the measuring method of the present invention by using Autoanalyzer Hitachi 7170 (mfd. by Hitachi Ltd.).

Samples

Five control sera.

Reagents

Reagent Solution 15
R-1: 25 mM TAPSO-NaOH buffer (pH 7.0) containing 5 U/ml of Co (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Emalgen 705 (a polyoxyethylene higher alcohol ether, a trade name, Kao Corporation) and 1,000 U/ml of CAT (available from Boehringer Mannheim Co., Ltd.).
R-2: 25 mM TAPSO-NaOH buffer (pH 7.0) containing 1 mM of 4-AA, 20 U/ml of POD (serial number PEO-302, available from TOYOBO Co., Ltd.), 0.5% (w/v) of Emalgen 709 (a polyoxyethylene higher alcohol ether, a trade name, Kao Corporation) and 0.1% (w/v) of NaN$_3$.

Reagent solution 16
R-1: 25 mM TAPSO-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Emalgen 705 (a polyoxyethylene higher alcohol ether, a trade name, Kao Corporation) and 2 U/ml of POD (serial number PEO-302, available from TOYOBO Co., Ltd.).
R-2: 25 mM TAPSO-NaOH buffer (pH 7.0) containing 1 mM of 4-AA and 0.5% (w/v) of Emalgen 709 (a polyoxyethylene higher alcohol ether, a trade name, Kao Corporation).

Measuring Conditions

The same as in Example 2.

Results

The results obtained are shown in Table 3.

TABLE 3

| Sample No. | Reagent solution 15 (mg/dl) | Reagent solution 16 (mg/dl) | Nominal value (mg/dl) |
|---|---|---|---|
| 1 | 58.3 | 55.4 | 52 |
| 2 | 98.9 | 93.9 | 98 |
| 3 | 129.8 | 125.5 | 130 |
| 4 | 183.3 | 180.3 | 191 |
| 5 | 220.6 | 215.7 | 218 |
| Mean value | 138.3 | 134.2 | 138 |

As is clear from the results shown in Table 3, the LDL-cholesterol values obtained by use of each of the reagents containing a polyanion and an amphoteric surfactant of the present invention (reagent solutions 15 and 16) are substantially equal to the nominal values of the control sera, values measured by BQ method (Beta quantification method).

EXAMPLE 4

The amount of LDL-cholesterol in control sera [available from PBI (Pacific Biometrics, Inc.] each having a known LDL-cholesterol value measured by BQ method (Beta quantification method) was measured by the measuring method of the present invention by using Autoanalyzer Hitachi 7170 (mfd. be Hitachi Ltd.).

Samples

The same as in Example 3.

Reagents

Reagent Solution 17
R-1: 25 mM 2-morpholinoethanesulfonic acid (MES)-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Triton X-100 (HLB: 13.5) and 1,000 U/ml of CAT (available from Boehringer Mannheim Co., Ltd.).
R-2: 25 mM MES-NaOH buffer (pH 7.0) containing 1 mM of 4-AA, 20 U/ml of POD (serial number PEO-302, available from TOYOBO Co., Ltd.), 0.5% (w/v) of Emalgen 709 (a polyoxyethylene higher alcohol ether, a trade name, Kao Corporation) and 0.1% (w/v) of NaN$_3$.

Reagent Solution 18
R-1: 25 mM TAPSO-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Emalgen 705 (a polyoxyethylene higher alcohol ether, a trade name, Kao Corporation) and 1,000 U/ml of CAT (available from Boehringer Mannheim Co., Ltd.).

R-2: 25 mM TAPSO-NaOH buffer (pH 7.0) containing 1 mM of 4-AA, 20 U/ml of POD (serial number PEO-302, available from TOYOBO Co., Ltd.), 0.5% (w/v) of Emalgen 709 (a polyoxyethylene higher alcohol ether, a trade name, Kao Corporation) and 0.1% (w/v) of $NaN_3$.

Reagent solution 19

R-1: 25 mM bis(2-hydroxyethyl)iminotris (hydroxymethyl)-methane (Bis-Tris)-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Triton X-100 (HLB: 13.5) and 1,000 U/ml of CAT (available from Boehringer Mannheim Co., Ltd.).

R-2: 25 mM Bis-Tris-NaOH buffer. (pH 7.0) containing 1 mM of 4-AA, 20 U/ml of POD (serial number PEO-302, available from TOYOBO Co., Ltd.), 0.5% of Triton X-100 and 0.1% (w/v) of $NaN_3$.

Measuring Conditions

The same as in Example 2.

Results

The results obtained are shown in Table 4.

TABLE 4

| Sample No. | Reagent solution 17 (mg/dl) | Reagent solution 18 (mg/dl) | Reagent solution 19 (mg/dl) | Nominal value (mg/dl) |
|---|---|---|---|---|
| 1 | 58.7 | 54.3 | 53.0 | 52 |
| 2 | 102.7 | 98.8 | 101.1 | 98 |
| 3 | 133.5 | 133.0 | 130.0 | 130 |
| 4 | 190.2 | 193.6 | 181.2 | 191 |
| 5 | 214.6 | 224.9 | 211.7 | 218 |
| Mean value | 139.9 | 140.9 | 135.4 | 138 |

As is clear from the results shown in Table 4, the LDL-cholesterol values obtained by use of each of the reagents containing a polyanion and an amphoteric surfactant of the present invention (reagent solutions 17 to 19) are substantially equal to the nominal values of the control sera, values measured by BQ method (Beta quantification method).

REFERENCE EXAMPLE 2

Modified antibodies were prepared by conventional processes.

(1) Preparation of Dextran-Modified Antibody

With 15 ml of sheep anti-HDL antibody (10 mg protein Ab/ml) was mixed 300 mg of dialdehyde dextran, and the reaction was carried out at 30° C. in 50 mM phosphate buffer (pH 6.0). Then, 200 mg of borane pyridine was added and the reaction was carried out for 5 hours. A cellophane filled with the reaction mixture, followed by desalting, and concentration by ultrafiltration. Thus, dextran-modified antibody (10 mg protein Ab/ml×12.6 ml) was obtained.

(2) Preparation of Heparin-Modified Antibody

To 100 mg of heparin subjected to periodate oxidation was added 50 mg of 6-aminocaproic acid, and the resulting mixture was dialyzed. To the dialyzed mixture were added 5 ml of sheep anti-HDL antibody (10 mg protein Ab/ml) and 300 mg of 1-ethyl-3-(3-dimethylaminopropyl)-carbodiimide, and the reaction was carried out overnight at 5° C. A cellophane tube was filled with the reaction mixture, followed by desalting, and concentration by ultrafiltration. Thus, heparin-modified antibody (10 mg protein Ab/ml×3.6 ml) was obtained.

(3) Preparation of Alginic Acid-Modified Antibody

In 20 ml of 20 mM phosphate buffer (pH 7.0) was dissolved 50 mg of alginic acid, followed by adding thereto 5 ml of sheep anti-HDL antibody (10 mg protein Ab/ml) and 500 mg of 1-ethyl-3-(3-dimethylaminopropyl)carbodiimide, and the reaction was carried out overnight at 5° C. A cellophane tube was filled with the reaction mixture, followed by desalting, and concentration by ultrafiltration. Thus, alginic acid-modified antibody (10 mg protein Ab/ml× 3.4 ml) was obtained.

(4) Preparation of Glucuronic Acid-Modified Antibody

In 0.1 M phosphate buffer (pH 7.0) were dissolved 10 ml of sheep anti-HDL antibody (10 mg protein Ab/ml) and 400 mg of glucuronic acid, followed by adding thereto 250 mg of cyanogen borohydride, and the reaction was carried out overnight at 37° C. for 5 hours. A cellophane tube was filled with the reaction mixture, followed by desalting, and concentration by ultrafiltration. Thus, glucuronic acid-modified antibody (10 mg protein Ab/ml×7.6 ml) was obtained.

(5) Preparation of Poly(Glutamic Acid)-Modified Antibody

In 4 ml of 20 mM phosphate buffer (pH 6.5) was dissolved 20 mg of a poly(glutamic acid), followed by adding thereto 1 ml of sheep anti-HDL antibody (10 mg protein Ab/ml) and 40 mg of 1-ethyl-3-(3-dimethylaminopropyl)-carbodiimide, and the reaction was carried out overnight at 5° C. A cellophane tube was filled with the reaction mixture, followed by desalting, and concentration by ultrafiltration. Thus, poly(glutamic acid)-modified antibody (10 mg protein Ab/ml×0.72 ml) was obtained.

(6) Preparation of Glycyrrhetinic Acid-Modified Antibody

In 2 ml of 50 mM phosphate buffer (pH 6.5) was dissolved 100 mg of glycyrrhetinic acid, and 100 mg of sodium periodate was added to the solution. The reaction was carried out at 5° C. for 24 hours, followed by desalting by use of a Sephadex G-25 column. The desalted solution was mixed with 10 ml of sheep anti-HDL antibody (10 mg protein Ab/ml), and the reaction was carried out at 30° C. for 48 hours. A cellophane tube was filled with the reaction mixture, followed by desalting, and concentration by ultrafiltration. Thus, glycyrrhetinic acid-modified antibody (10 mg protein Ab/ml×7.3 ml) was obtained.

EXAMPLE 5

LDL-cholesterol values were measured by the measuring method of the present invention by using Autoanalyzer Hitachi 7170 (mfd. by Hitachi Ltd.), and the measured values were compared with LDL-cholesterol values measured by BQ method, a reference method.

Samples

As samples, there were used 15 human sera (triglycerides: less than 400 mg/dl) and 8 human sera (triglycerides: more than 400 mg/dl) [available from PBI (Pacific Biometrics, Inc.)] which each had a known LDL-cholesterol value measured by BQ method (Beta quantification method).

The amounts of serum triglycerides shown in Tables 5 and 6 are the nominal values of the human sera.

Reagents

Reagent Solution 20

R-1: 25 mM TAPSO-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Triton X-100 (HLB: 13.5) and 1,000 U/ml of CAT (available from Boehringer Mannheim Co., Ltd.).

R-2: 25 mM TAPSO-NaOH buffer (pH 7.0) containing 1 mM of 4-AA, 20 U/ml of POD (serial number PEO-302, available from TOYOBO Co., Ltd.), 0.5% (w/v) of Triton X-100 and 0.1% (w/v) of $NaN_3$.

Reagent Solution 21

R-1: 25 mM TAPSO-NaOH buffer (pH 7.0) containing 5 U/ml of CO (CHO "Amano VW", available from Amano Pharmaceutical Co., Ltd.), 5 U/ml of CHE (serial number T-18, available from Asahi Kasei Kogyo K.K.), 1 mM of HDAOS, 0.04% (w/v) of LEBON LAG 40, 0.03% (w/v) of heparin, 0.02% of Triton X-100 (HLB: 13.5), 1,000 U/ml of CAT (available from Boehringer Mannheim Co., Ltd.), and the sheep glucuronic acid-modified HDL antibody obtained in Reference Example 1, (4).

R-2: the same as in reagent solution 20.

Measuring Conditions

The same as in Example 2.

Results

Table 5 shows the results obtained from the sera having a triglycerides value of less than 400 mg/dl, and Table 6 the results obtained from the sera having a triglycerides value of more than 400 mg/dl.

TABLE 5

| Sample No. | Reagent solution 20 (mg/dl) | Reagent solution 21 (mg/dl) | Nominal value of LDL-cholesterol (mg/dl) | Nominal value of triglycerides (mg/dl) |
|---|---|---|---|---|
| 1 | 77 | 75 | 79 | 55 |
| 2 | 80 | 79 | 82 | 81 |
| 3 | 88 | 87 | 92 | 61 |
| 4 | 99 | 98 | 106 | 84 |
| 5 | 120 | 121 | 115 | 220 |
| 6 | 120 | 121 | 117 | 175 |
| 7 | 116 | 115 | 118 | 109 |
| 8 | 126 | 125 | 120 | 150 |
| 9 | 125 | 127 | 132 | 146 |
| 10 | 133 | 133 | 137 | 155 |
| 11 | 135 | 135 | 141 | 201 |
| 12 | 144 | 144 | 142 | 255 |
| 13 | 141 | 142 | 146 | 246 |
| 14 | 154 | 153 | 152 | 203 |
| 15 | 158 | 158 | 167 | 180 |
| Mean value | 121 | 121 | 123 | — |
| Coefficient of correlation with nominal value | 0.983 | 0.984 | — | — |

TABLE 6

| Sample No. | Reagent solution 20 (mg/dl) | Reagent solution 21 (mg/dl) | Nominal value of LDL-cholesterol (mg/dl) | Nominal value of triglycerides (mg/dl) |
|---|---|---|---|---|
| 1 | 58 | 55 | 54 | 409 |
| 2 | 102 | 88 | 60 | 754 |
| 3 | 125 | 117 | 104 | 490 |
| 4 | 130 | 120 | 108 | 720 |
| 5 | 112 | 111 | 109 | 404 |
| 6 | 109 | 107 | 110 | 431 |
| 7 | 134 | 127 | 129 | 445 |
| 8 | 146 | 138 | 135 | 501 |
| Mean value | 115 | 108 | 101 | — |
| Coefficient of correlation with nominal value | 0.874 | 0.936 | — | — |

From the results shown in Table 5, it can be seen that when the sera having a triglycerides value of less than 400 mg/dl are used as samples, both their LDL-cholesterol values measured by use of reagent solution 20 and those measured by use of reagent solution 21 are substantially equal to the nominal values measured by BQ method (Beta quantification method). From the results shown in Table 6, it can be seen that when the sera having a triglycerides value of more than 400 mg/dl are used as samples, the LDL-cholesterol values measured by use of reagent solution 21, i.e., those measured in the presence of not only a polyanion and an amphoteric surfactant but also an antibody capable of binding to lipoproteins other than LDL are closer to the nominal values, namely, reagent solution 21 makes it possible to measure LDL-cholesterol more specifically.

As described above, the present invention provides a method which makes it possible to measure LDL-cholesterol in a sample derived from a living body, specifically with high precision, and a reagent and a reagent composition which are used in said method. The application of the present invention permits direct measurement of LDL-cholesterol by use of a generally used autoanalyzer which has been impossible for a conventional method.

What is claimed is:

1. A method for measuring the amount of cholesterol in low density lipoproteins in a sample, which comprises contacting the sample with one or more reagent solutions to carry out the reaction in the presence of a polyanion and an amphoteric surfactant, and subjecting the reaction product obtained above to an optical measurement to determine the amount of cholesterol.

2. The method according to claim 1, wherein the optical measurement is conducted by measuring an absorbance ($OD_1$) of the solution obtained by contacting the sample with a first reagent solution, and measuring an absorbance ($OD_2$) of the solution obtained by contacting the solution for measuring $OD_1$ after measurement of $OD_1$ with a second reagent solution.

3. The method according to claim 2, wherein the first agent solution comprises (a) a polyanion and an amphoteric surfactant, (b) cholesterol esterase, (c-i) cholesterol oxidase, peroxidase and an oxidizable color producing reagent or (c-ii) cholesterol dehydrogenase and nicotinamide adenine dinucleotide (phosphate), and (d) an aqueous medium, and the second reagent solution comprises an aqueous medium.

4. The method according to claim 2, wherein the first reagent solution comprises (a) a polyanion and an amphoteric surfactant, (b) cholesterol esterase, (c) cholesterol oxidase, (d) peroxidase, and (e) an aqueous medium, and the second reagent solution comprises an aqueous medium, one of a coupler and a developer being contained in the first reagent solution, and the other being contained in the second reagent solution.

5. The method according to claim 2, wherein the first reagent solution comprises (a) a polyanion and an amphoteric surfactant, (b) cholesterol esterase, (c) cholesterol oxidase, (d) catalase, and (e) an aqueous medium, and the second reagent solution comprises (f) a catalase inhibitor and (g) an aqueous medium, each of peroxidase, a coupler and a developer being contained in at least one of the first reagent solution and the second reagent solution.

6. The method according to claim 2, wherein the first reagent solution comprises (a) a polyanion and an amphoteric surfactant, (b) cholesterol esterase, (c) cholesterol dehydrogenase and nicotinamide adenine dinucleotide (phosphate), and (d) an aqueous medium, and the second reagent solution comprises (e) an aqueous medium, and (f) cholesterol oxidase, peroxidase, an oxidizable color producing reagent and a cholesterol dehydrogenase inhibitor.

7. The method according to claim 2, wherein the first reagent solution comprises (a) a polyanion and an amphoteric surfactant, (b) cholesterol esterase, (c) cholesterol oxidase, peroxidase and at least one of a coupler and a developer, and (d) an aqueous medium, and the second reagent solution comprises (e) an aqueous medium, and (f) cholesterol dehydrogenase, nicotinamide adenine dinucleotide (phosphate) and a cholesterol oxidase inhibitor.

8. The method according to claim 2, wherein the measurement of the absorbance $OD_1$ is conducted in a period after substantial completion of the reaction of the cholesterol in liporoteins other than low density lipoproteins and before the initiation of the reaction of the cholesterol in low density lipoproteins, and the measurement of the absorbance $OD_2$ is conducted after substantial completion of the reaction of cholesterol in low density lipoproteins.

9. The method according to claim 1, wherein the reagent solution comprises (a) a polyanion and an amphoteric surfactant, (b) cholesterol esterase, (c-i) cholesterol oxidase, peroxidase and an oxidizable color producing reagent, or (c-ii) cholesterol dehydrogenase and nicotinamide adenine dinucleotide (phosphate), and (d) an aqueous medium, and optical measurement is conducted by measuring an absorbance $OD_1$ in a period after substantial completion of the reaction of the cholesterol in the lipoproteins other than low density lipoproteins but before the initiation of the reaction of the cholesterol in low density lipoproteins with the reagent solution, and an absorbance $OD_2$ is measured after substantial completion of the reaction of cholesterol in low density lipoproteins with the reagent solution.

10. A reagent for measuring the amount of cholesterol in low density lipoproteins, which comprises (a) cholesterol esterase and cholesterol oxidase or cholesterol dehydrogenase, (b) a polyanion, and (c) an amphoteric surfactant.

11. A kit for measuring the amount of cholesterol in low density lipoproteins, which comprises:
(A) a first reagent container containing (a) a polyanion, (b) an amphoteric surfactant, (c) cholesterol esterase, (d-i) cholesterol oxidase, peroxidase and an oxidizable color producing reagent or (d-ii) cholesterol dehydrogenase and nicotinamide adenine dinucleotide (phosphate), and (e) an aqueous medium, and
(B) a second reagent container containing an aqueous medium.

12. A kit for measuring the amount of cholesterol in low density lipoproteins, which comprises:
(A) a first reagent container containing (a) a polyanion, (d) an amphoteric surfactant, (c) cholesterol esterase, (d) cholesterol oxidase, (e) peroxidase, and (f) an aqueous medium, and
(B) a second reagent container containing an aqueous medium,
wherein one of a coupler and a developer is further incorporated in the first reagent container, and the other is incorporated in the second reagent container.

13. A kit for measuring the amount of cholesterol in low density lipoproteins, which comprises:
(A) a first reagent container containing (a) a polyanion, (b) an amphoteric surfactant, (c) cholesterol esterase, (d) cholesterol oxidase, (e) catalase, and (f) an aqueous medium,
(B) a second reagent container containing (g) a catalase inhibitor and (h) an aqueous medium,
wherein each of peroxidase, a coupler and a developer is incorporated in at least one of the first reagent container and the second reagent container.

14. A kit for measuring the amount of cholesterol in low density lipoproteins, which comprises:
(A) a first reagent container containing (a) a polyanion, (b) an amphoteric surfactant, (c) cholesterol esterase, (d) cholesterol dehydrogenase, (e) nicotinamide adenine dinucleotide (phosphate), and (f) an aqueous medium,
(B) a second reagent container containing (g) an aqueous medium and (h) cholesterol oxidase, (i) peroxidase, (j) an oxidizable color producing reagent, and (k) a cholesterol dehydrogenase inhibitor.

15. A kit for measuring the amount of cholesterol in low density lipoproteins, which comprises:
(A) a first reagent container containing (a) a polyanion, (b) an amphoteric surfactant, (c) cholesterol esterase, (d) cholesterol oxidase, (e) peroxidase, (f) at least one of a coupler and a developer, and (g) an aqueous medium,
(B) a second reagent container containing (h) an aqueous medium, (i) cholesterol dehydrogenase, (j) nicotinamide adenine dinucleotide (phosphate) and (k) a cholesterol oxidase inhibitor.

16. A reagent composition for measuring the amount of cholesterol in low density lipoproteins, which comprises:
(a) a polyanion, (b) an amphoteric surfactant, (c) cholesterol esterase, (d-i) cholesterol oxidase, peroxidase and an oxidizable color producing reagent or (d-ii) cholesterol dehydrogenase and nicotinamide adenine dinucleotide (phosphate), and (e) an aqueous medium.

17. The method according to claim 1, wherein the sample is contacted with one or more reagent solutions in the presence of an antibody binding to the lipoproteins other than low density lipoproteins.

18. The method according to claim 1, wherein the sample is contacted with one or more reagent solutions in the presence of a nonionic surfactant and/or an anionic surfactant.

19. The method according to claim 1, wherein the amphoteric surfactant is at least one compound selected from the group consisting of alkyl betaine derivatives, imidazolinium betaine derivatives, sulfobetaine derivatives, aminocarboxylic acid derivatives, imidazoline derivatives and amine oxide derivatives.

20. The method according to claim 1, wherein the amphoteric surfactant is at least one compound selected from the group consisting of lauryl betaine, lauric acid amidopropyl betaine, coconut oil fatty acid amidopropyl betaine, 2-alkyl-N-carboxymethyl-N-hydroxyethyl imidazolinium betaine and 2-alkyl-N-carboxyethyl-N-hydroxyethyl imidazolinium betaine.

21. The method according to claim 1, wherein the polyanion is at least one compound selected from the group consisting of heparin, phosphotungstic acid, dextran sulfate, sulfated cyclodextrin, heparan sulfate, chondroitin sulfate, hyaluronic acid, sulfated oligosaccharide, sulfated polyactylamide, carboxymethylated polyactylamide and a salt thereof.

22. The reagent according to claim 10, wherein the reagent further incorporates an antibody binding to the lipoproteins other than low density lipoproteins.

23. The reagent according to claim 10, wherein the reagent further incorporates a nonionic surfactant and/or an anionic surfactant.

24. The reagent according to claim 10, wherein the amphoteric surfactant is at least one compound selected from the group consisting of alkyl betaine derivatives, imidazolinium betaine derivatives, sulfobetaine derivatives, aminocarboxylic acid derivatives, imidazoline derivatives and amine oxide derivatives.

25. The reagent according to claim 10, wherein the amphoteric surfactant is at least one compound selected from the group consisting of lauryl betaine, lauric acid amidopropyl betaine, coconut oil fatty acid amidopropyl betaine, 2-alkyl-N-carboxymethyl-N-hydroxyethyl imidazolinium betaine and 2-alkyl-N-carboxyethyl-N-hydroxyethyl imidazolinium betaine.

26. The reagent according to claim 10, wherein the polyanion is at least one compound selected from the group consisting of heparin, phosphotungstic acid, dextran sulfate, sulfated cyclodextrin, heparan sulfate, chondroitin sulfate, hyaluronic acid, sulfated oligosaccharide, sulfated polyactylamide, carboxymethylated polyactylamide and a salt thereof.

27. The kit according to claim 13, wherein the first reagent container further incorporates an antibody binding to the lipoproteins other than low density lipoproteins.

28. The kit according to claim 13, wherein at least one of the first reagent container and the second reagent container further incorporates a nonionic surfactant and/or an anionic surfactant.

29. The kit according to claim 13, wherein the amphoteric surfactant is at least one compound selected from the group consisting of alkyl betaine derivatives, imidazolinium betaine derivatives, sulfobetaine derivatives, aminocarboxylic acid derivatives, imidazoline derivatives and amine oxide derivatives.

30. The kit according to claim 13, wherein the amphoteric surfactant is at least one compound selected from the group consisting of lauryl betaine, lauric acid amidopropyl betaine, coconut oil fatty acid amidopropyl betaine, 2-alkyl-N-carboxymethyl-N-hydroxyethyl imidazolinium betaine and 2-alkyl-N-carboxyethyl-N-hydroxyethyl imidazolinium betaine.

31. The reagent according to claim 13, wherein the polyanion is at least one compound selected from the group consisting of heparin, phosphotungstic acid, dextran sulfate, sulfated cyclodextrin, heparan sulfate, chondroitin sulfate, hyaluronic acid, sulfated oligosaccharide, sulfated polyactylamide, carboxymethylated polyactylamide and a salt thereof.

32. A method for measuring an amount of cholesterol in low density lipoproteins in a sample, which comprises contacting the sample with (a) cholesterol esterase, cholesterol oxidase, peroxidase and an oxidizable color producing reagent or (b) cholesterol esterase, cholesterol dehydrogenase and nicotinamide adenine dinucleotide (phosphate) to cause a reaction, in the presence of a polyanion and an amphoteric surfactant, whereby a dye or reduced nicotinamide adenine dinucleotide (phosphate) is produced, measuring an amount of the dye or reduced nicotinamide adenine dinucleotide (phosphate), and determining the amount of cholesterol on the basis of the above-measured amount, whereby the amount of cholesterol in a low density lipoprotein in the sample is specifically measured.

33. The method according to claim 32, wherein the amount of the dye or reduced nicotinamide adenine dinucleotide (phosphate) is determined by measuring an absorbance of the reaction solution.

* * * * *